United States Patent
Carpenter et al.

(10) Patent No.: US 10,351,821 B2
(45) Date of Patent: *Jul. 16, 2019

(54) NEURAL CELL POPULATIONS FROM PRIMATE PLURIPOTENT STEM CELLS

(71) Applicant: Asterias Biotherapeutics, Inc., Fremont, CA (US)

(72) Inventors: Melissa K. Carpenter, Castro Valley, CA (US); R. Scott Thies, Pleasanton, CA (US)

(73) Assignee: Asterias Biotherapeutics Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/785,029

(22) Filed: Oct. 16, 2017

(65) Prior Publication Data

US 2018/0291337 A1    Oct. 11, 2018

Related U.S. Application Data

(60) Continuation of application No. 13/561,296, filed on Jul. 30, 2012, now Pat. No. 9,790,466, which is a continuation of application No. 12/477,726, filed on Jun. 3, 2009, now Pat. No. 8,252,586, which is a continuation of application No. 11/010,230, filed on Dec. 10, 2004, now Pat. No. 7,560,281, which is a division of application No. 09/888,309, filed on Jun. 21, 2001, now abandoned, which is a continuation-in-part of application No. 10/873,414, filed on Jun. 21, 2004, now abandoned.

(60) Provisional application No. 60/220,064, filed on Jul. 21, 2000, provisional application No. 60/216,387, filed on Jul. 7, 2000, provisional application No. 60/213,740, filed on Jun. 22, 2000, provisional application No. 60/213,739, filed on Jun. 22, 2000.

(51) Int. Cl.
*A61K 35/12* (2015.01)
*C12N 5/0735* (2010.01)
*C12N 15/10* (2006.01)

(52) U.S. Cl.
CPC ....... *C12N 5/0606* (2013.01); *C12N 15/1034* (2013.01); *C12N 15/1072* (2013.01); *C12N 15/1096* (2013.01); *A61K 35/12* (2013.01); *C12N 2500/14* (2013.01); *C12N 2500/30* (2013.01); *C12N 2500/38* (2013.01); *C12N 2500/44* (2013.01); *C12N 2500/62* (2013.01); *C12N 2501/105* (2013.01); *C12N 2501/13* (2013.01); *C12N 2501/155* (2013.01); *C12N 2501/385* (2013.01); *C12N 2501/39* (2013.01); *C12N 2501/999* (2013.01); *C12N 2502/13* (2013.01); *C12N 2502/99* (2013.01); *C12N 2503/02* (2013.01); *C12N 2510/00* (2013.01); *C12N 2510/04* (2013.01); *C12N 2533/90* (2013.01)

(58) Field of Classification Search
CPC .............. C12N 5/0606; C12N 15/1034; C12N 15/1072; C12N 15/1096; C12N 2500/14; C12N 2500/30; C12N 2500/44; C12N 2500/62; C12N 2501/105; C12N 2501/13; C12N 2501/155; C12N 2501/385; C12N 2501/39; C12N 2501/999; C12N 2502/13; C12N 2502/99; C12N 2503/02; C12N 2510/00; C12N 2510/04; C12N 2533/90; A61K 35/12; C12M 2500/38
See application file for complete search history.

(56) References Cited

U.S. PATENT DOCUMENTS

| | | |
|---|---|---|
| 5,411,883 A | 5/1995 | Boss et al. |
| 5,639,618 A | 6/1997 | Gay |
| 5,672,499 A | 9/1997 | Anderson et al. |
| 5,766,948 A | 6/1998 | Gage et al. |
| 5,773,255 A | 6/1998 | Laurance et al. |
| 5,789,246 A | 8/1998 | Reid et al. |
| 5,849,553 A | 12/1998 | Anderson et al. |
| 5,851,832 A | 12/1998 | Weiss et al. |
| 5,928,947 A | 7/1999 | Anderson et al. |

(Continued)

FOREIGN PATENT DOCUMENTS

| | | |
|---|---|---|
| AU | 751321 | 8/2002 |
| EP | 1022330 | 7/2000 |

(Continued)

OTHER PUBLICATIONS

Wakefield et al., Nature, 13: 326-341, 2013.*

(Continued)

*Primary Examiner* — Thaian N Ton
(74) *Attorney, Agent, or Firm* — Krista P. Kauppinen

(57) ABSTRACT

This invention provides a system for efficiently producing differentiated cells from pluripotent cells, such as human embryonic stem cells. Rather than permitting the cells to form embryoid bodies according to established techniques, differentiation is effected directly in monolayer culture on a suitable solid surface. The cells are either plated directly onto a differentiation-promoting surface, or grown initially on the solid surface in the absence of feeder cells and then exchanged into a medium that assists in the differentiation process. The solid surface and the culture medium can be chosen to direct differentiation down a particular pathway, generating a cell population that is remarkably uniform. The methodology is well adapted to bulk production of committed precursor and terminally differentiated cells for use in drug screening or regenerative medicine.

10 Claims, 5 Drawing Sheets

Figure 1:
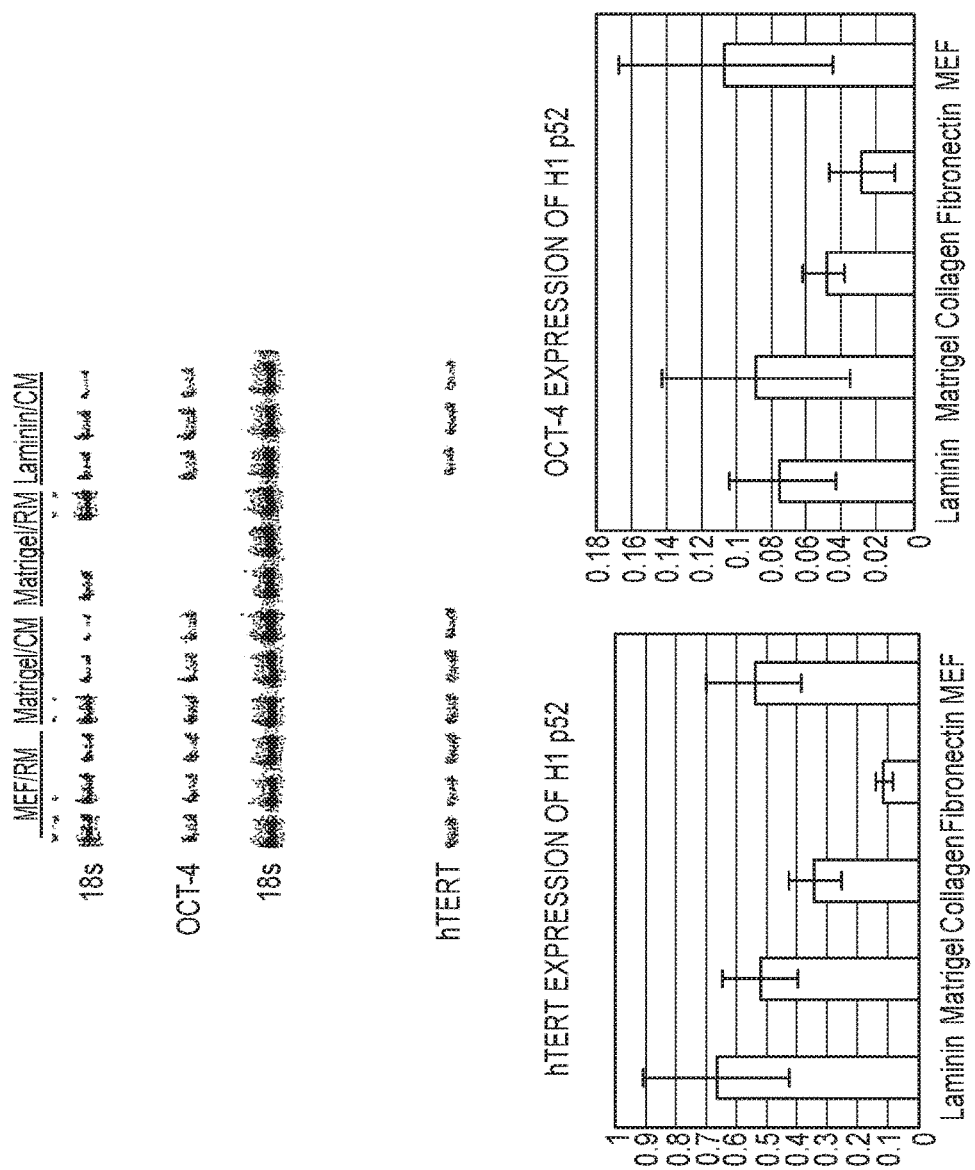

Specification includes a Sequence Listing.

(56) References Cited

U.S. PATENT DOCUMENTS

| | | | |
|---|---|---|---|
| 5,968,829 | A | 10/1999 | Carpenter |
| 5,981,165 | A | 11/1999 | Weiss et al. |
| 6,040,180 | A | 3/2000 | Johe |
| 6,087,168 | A | 7/2000 | Levesque et al. |
| 6,090,622 | A | 7/2000 | Gearhart et al. |
| 6,200,806 | B1 | 3/2001 | Thomson |
| 6,238,922 | B1 | 5/2001 | Uchida |
| 6,458,589 | B1 | 10/2002 | Rambhatla et al. |
| 6,602,711 | B1 | 8/2003 | Thomson et al. |
| 6,686,198 | B1 | 2/2004 | Melton et al. |
| 6,833,269 | B2 | 12/2004 | Carpenter |
| 7,250,294 | B2 | 7/2007 | Carpenter et al. |
| 7,560,281 | B2 | 7/2009 | Carpenter et al. |
| 2002/0009743 | A1 | 1/2002 | Carpenter |
| 2002/0012903 | A1 | 1/2002 | Goldman et al. |
| 2002/0019046 | A1 | 2/2002 | Carpenter |
| 2002/0022267 | A1 | 2/2002 | Pera |
| 2002/0039724 | A1 | 4/2002 | Carpenter |
| 2002/0068045 | A1 | 6/2002 | Reubinoff et al. |
| 2002/0151056 | A1 | 10/2002 | Sasal et al. |
| 2003/0113910 | A1 | 6/2003 | Levanduski |
| 2004/0023376 | A1 | 2/2004 | Thomson et al. |
| 2005/0042749 | A1 | 2/2005 | Carpenter et al. |
| 2005/0095707 | A1 | 5/2005 | Carpenter et al. |
| 2006/0078545 | A1 | 4/2006 | Carpenter |
| 2007/0009491 | A1 | 1/2007 | Weiss et al. |
| 2009/0291495 | A1 | 11/2009 | Carpenter et al. |

FOREIGN PATENT DOCUMENTS

| | | |
|---|---|---|
| EP | 605428 | 4/2002 |
| EP | 592521 | 5/2003 |
| EP | 594669 | 5/2003 |
| WO | 1994003199 | 2/1994 |
| WO | 19980030678 | 7/1998 |
| WO | 19980050526 | 11/1998 |
| WO | 1999001159 | 1/1999 |
| WO | 19990004775 | 2/1999 |
| WO | 19990020741 | 4/1999 |
| WO | 19990028443 | 6/1999 |
| WO | 19990043785 | 9/1999 |
| WO | 19990053021 | 10/1999 |
| WO | 19990053022 | 10/1999 |
| WO | 2000009668 | 2/2000 |
| WO | 20000017323 | 3/2000 |
| WO | 20000047762 | 8/2000 |
| WO | 20010000650 | 1/2001 |
| WO | 20010051616 | 7/2001 |
| WO | 20010068815 | 9/2001 |
| WO | 20010083715 | 11/2001 |
| WO | 20010088104 | 11/2001 |
| WO | 20010098463 | 12/2001 |
| WO | 20020081663 | 10/2002 |
| WO | 20020086106 | 10/2002 |
| WO | 20040007696 | 1/2004 |

OTHER PUBLICATIONS

Dr. Lyle Armstrong to the UK House of Parliaments' Select Committee on Science and Technology, Fifth Report of Session 2006-07, vol. II, pp. 76-77, Apr. 5, 2007.
Lai et. al., Proc Natl Acad Sci USA, Mar. 6, 2012; 109(10):3772-7.
Dominguez-Bendala et. al., Handbook of Stem Cells, Chapter 70: Islet Cell Therapy and Pancreatic Stem Cells, pp. 835-853, 2013.
Salehi et. al., Int. J. Dev. Biol., 55:321-326, 2011.
Zwaka and Thomson, "A Germ Cell Origin of Embryonic Stem Cells?" 2005 Development 132:227-233.
Reijo et. al. 2009, Differentiation, vol. 78, pp. 18-23.
"Neural Implant Technologies," NeuroInvestment website (Dec. 1999) 17 pp.
Amit, M. et. al., "Clonally Derived Human Embryonic Stem Cell Lines Maintain Pluripotency and Proliferative Potential for Prolonged Periods of Culture," Dev. Biol. 227, (2000), pp. 271-278.
Andrews, P., "Retinoic Acid Induces Neuronal Differentiation of a Cloned Human Embryonal Carcinoma Cell Line In Vitro," Dev. Biol. 103, (1984), pp. 285-293.
Bain, G. et. al., "Embryonic Stem Cells Express Neuronal Properties In Vitro," Dev. Biol. 168, (1995), pp. 342-357.
Bain, G. et. al., "Expression of Retinoid X Receptors in P19 Embryonal Carcinoma Cells and Embryonic Stem Cells," Biochem. Biophys. Res. Comm. 200(3), (1994), pp. 1252-1256.
Bain, G. et. al., "Neural Cells Derived by In Vitro Differentiation of P19 and Embryonic Stem Cells," Perspect. Dev. Neurobiol. 5, (1998), pp. 175-178.
Bain, G. et. al., "Retinoic Acid Promotes Neural and Represses Mesodermal Gene Expression in Mouse Embryonic Stem Cells in Culture," Biochem. Biophys. Res. Comm. 223, (1996), pp. 691-694.
Bhatia, M. et. al., "Bone Morphogenetic Proteins Regulate the Developmental Program of Human Hematopoietic Stem Cells," J. Exp. Med. 189, (1999), pp. 1139-1147.
Biesecker, L. et. al., "Interleukin-6 is a Component of Human Umbilical Cord Serum and Stimulates Hematopoiesis in Embryonic Stem Cells In Vitro," Exp. Hematol. 21, (1993), pp. 774-778.
Bodnar, A. et. al., "Extension of Life-Span by Introduction of Telomerase Into Normal Human Cells," Science 279, (1998), pp. 349-352.
Bouwmeester, T. et. al., "Vertebrate Head Induction by Anterior Primitive Endoderm," BioEssays 19(10), (1997), pp. 855-863.
Brustle, O. et. al., "Embryonic Stem Cell-Derived Glial Precursors: A Source of Myelinating Transplants," Science 285, (1999), pp. 754-756.
Brustle, O. et. al., "In Vitro Generated Neural Precursors Participate in Mammalian Brain Development," Proc. Natl. Acad. Sci. USA 94, (1997), pp. 14809-14814.
Burkert, U. et. al., "Early Fetal Hematopoietic Development from In Vitro Differentiated Embryonic Stem Cells," New Biol. 3(7), (1991), pp. 698-708.
Caldwell, M. et. al., "Growth Factors Regulate the Survival and Fate of Cells Derived from Human Neurospheres," Nature Biotech. 19, (2001), pp. 475-479.
Carpenter, M. et. al., "Enrichment of Neurons and Neural Precursors from Human Embryonic Stem Cells," Exp. Neurol. 172(2), (2001), pp. 383-397.
Carpenter, M. et. al., "In Vitro Expansion of a Multipotent Population of Human Neural Progenitor Cells," Exp. Neurol. 158, (1999), pp. 265-278.
Chitnis, A. et. al., "Neural Induction and Neurogenesis in Amphibian Embryos," Perspectives Dev. Neurobiol. 3(1), (1995), pp. 3-15.
Church, V. et. al., "Different Effects of BMP Antagonists Noggin and Fetuin on the Osteogenic Differentiation of Human Marrow Mesenchymal Stem Cells," Calcified Tissue Intl. 64 (Suppl. 1), Abstract No. P-17, (1999), S54.
Cibelli, J. et. al., "Parthenogenic Stem Cells in Nonhuman Primates," Science 295, (2002), p. 819.
Clarke, D. et. al., "Generalized Potential of Adult Neural Stem Cells," Science 288, (2000), pp. 1660-1663.
Davidson, B. et. al. "Cell Fate and Lineage Specification in the Gastrulating Mouse Embryo," Cell Lineage & Fate Determination 33, (1999), pp. 491-504.
Deacon, T. et. al., "Blastula-Stage Stem Cells Can Differentiate Into Dopaminergic and Serotonergic Neurons After Transplantation," Exp. Neurol. 149, (1998), pp. 28-41.
Dinsmore, J. et. al., "Embryonic Stem Cells Differentiated In Vitro as a Novel Source of Cells for Transplantation," Cell Transpl. 5(2), (1996), pp. 131-143.
Du, Z-W et. al., "Neural Differentiation from Embryonic Stem Cells: Which Way?" Stem Cells & Dev. 13, (2004), pp. 372-381.
Fisher, J. et. al., "Factors Influencing the Differentiation of Embryonal Carcinoma and Embryo-Derived Stem Cells," Exp. Cell Res. 182, (1989), pp. 403-414.
Fraichard, A. et. al., "In Vitro Differentiation of Embryonic Stem Cells into Glial Cells and Functional Neurons," J. Cell Sci. 108, (1995), pp. 3181-3188.

(56) References Cited

OTHER PUBLICATIONS

Gard, A. "Oligodendrocyte Progenitors Isolated Directly from Developing Telencephalon at a Specific Phenotype Stage: Myelinogenic Potential in a Defined Environment," Development 106, (1989), pp. 119-132.
Gendron, R. et. al., "Induction of Embryonic Vasculogenesis by bFGF and LIF In Vitro and In Vivo," Dev. Biol. 177, (1996), pp. 332-346.
Ginis, I. et. al., "Differences Between Human and Mouse Embryonic Stem Cells," Dev. Biol. 269, (2004), pp. 360-380.
Goldman, J. et. al., "Differentiation of Astrocytes and Oligodendrocytes from Germinal Matrix Cells in Primary Culture," J. Neurosci. 6(1), (1986), pp. 52-60.
Itskovitz-Eldor, J. et. al., "Differentiation of Human Embryonic Stem Cells Into Embryoid Bodies Comprising the Three Embryonic Germ Layers," Mol. Med. 6(2), (2000), pp. 88-95.
Jain, K., "Ethical and Regulatory Aspects of Embryonic Stem Cell Research," Expert Opin. Biol. Ther. 2, (2002), pp. 819-826.
Juul, S. et. al., "Erythropoietin and Erythropoietin Receptor in the Developing Human Central Nervous System," Pediatr. Res. 43, (1998), pp. 40-49.
Kalyani, A. et. al., "Cell Lineage in the Developing Neural Tube," Biochem. Cell Biol. 76, (1998), pp. 1051-1068.
Kawasaki, H. et. al., "Generation of Dopaminergic Neurons and Pigmented Epithelia from Primate ES Cells by Stromal Cell-Derived Inducing Activity," Proc. Natl. Acad. Sci. USA 99, (2002), pp. 1580-1585.
Kawasaki, H. et. al., "Induction of Midbrain Dopaminergic Neurons from ES Cells by Stromal Cell-Derived Inducing Activity," Neuron 28(1), (2000), pp. 31-40.
Kawase, E. et. al., "Mouse Embryonic Stem (ES) Cell Lines Established from Neuronal Cell-Derived Cloned Blastocysts," Genesis 28, (2000), pp. 156-163.
Keller, G. "In Vitro Differentiation of Embryonic Stem Cells," Curr. Opin. Cell Biol. 7(6), (1995), pp. 862-869.
Kleinert, R. "Immunohistochemical Characterization of Primitive Neuroectodermal Tumors and Their Possible Relationship to the Stepwise Ontogenetic Development of the Central Nervous System," Acta Neuropathol. 82, (1991), pp. 502-507.
Lamb, T. et. al., "Neural Induction by the Secreted Polypeptide Noggin," Science 262, (1993), pp. 713-718.
Lee, S-H et. al., "Efficient Generation of Midbrain and Hindbrain Neurons from Mouse Embryonic Stem Cells," Nat. Biotech. 18, (2000), pp. 675-679.
Levinson-Dushnik, M. et. al., "Involvement of Hepatocyte Nuclear Factor 3 in Endoderm Differentiation of Embryonic Stem Cells," Mol. Cell Biol. 17(7), (1997), pp. 3817-3822.
Van Inzen, W. et. al., "Neuronal Differentiation of Embryonic Stem Cells," Biochim. Biophys. Acta 1312, (1996), pp. 21-26.
Varlet, I. et. al., "Nodal Expression in the Primitive Endoderm is Required for Specification of the Anterior Axis During Mouse Gastrulation," Development 124, (1997), pp. 1033-1044.
Verfaillie, C. et. al., "Stem Cells: Hype and Reality," Hematology Am. Soc. Hematol. Educ. Program, (2002), pp. 369-391.
Vescovi, A. et. al., "Isolation and Cloning of Multipotential Stem Cells from the Embryonic Human CNS and Establishment of Transplantable Human Neural Stem Cell Lines by Epigenetic Stimulation," Exp. Neurol. 156, (1999), pp. 71-83.
Vogel, G., "Breakthrough of the Year: Capturing the Promise of Youth," Science 286, (1999), pp. 2238-2239.
Wagner, J. et. al., "Induction of a Midbrain Dopaminergic Phenotype in Nurr1-overexpressing Neural Stem Cells by Type 1 Astrocytes," Nature Biotech. 17, (1999), pp. 653-659.
Walters, A. et. al., "The Properties of Cultured Fetal Human and Rat Brain Tissue and Its Use as Grafts for the Relief of the Parkinsonian Syndrome," Neurochem. Res. 17(9), (1992), pp. 893-900.
Wang, Q. et. al., "Identification of an Activin-Follistatin Growth Modulatory System in the Human Prostate: Secretion and Biological Activity in Primary Cultures of Prostatic Epithelial Cells," J. Urol. 161, (1999), pp. 1378-1384.
Wang, S. et. al., "Neural Cells Derived in Culture from Human Embryonic Germ (EG) Cells," Mol. Biol. Cell 9, (1998), 437A.
Wells, D. et. al., Preimplantation Genetic Diagnosis: Applications for Molecular Medicine, Trends Molec. Med. 7(1), (2001), pp. 23-30.
Wilton, L. et. al., "Biopsy of Preimplantation Mouse Embryos: Development of Micromanipulated Embryos and Proliferation of Single Blastomeres In Vitro," Biol. Reprod. 40, (1989), pp. 145-152.
Wobus, A. et. al., "Specific Effects of Nerve Growth Factor on the Differentiation Pattern of Mouse Embryonic Stem Cells In Vitro," Biomed. Biochim. Acta 47(12), (1988), pp. 965-973.
Wojcik, B. et. al., "Catecholaminergic Neurons Result from Intracerebral Implantation of Embryonal Carcinoma Cells," Proc. Natl. Acad. Sci. USA 90, (1993), pp. 1305-1309.
Xu, C. et. al. "Feeder-Free Growth of Undifferentiated Human Embryonic Stem Cells," Nature Biotech. 19, (2001), pp. 971-974.
Yandava, B. et. al., "'Global' Cell Replacement is Feasible via Neural Stem Cell Transplantation: Evidence from the Dysmyelinated Shiverer Mouse Brain," Proc. Natl. Acad. Sci. USA 96, (1999), pp. 7029-7034.
Yao, M. et. al., "Neuronal Differentiation of P19 Embryonal Carcinoma Cells in Defined Media," J. Neurosci. Res. 41, (1995), pp. 792-804.
Zhang, S-C et. al., "In Vitro Differentiation of Transplantable Neural Precursors from Human Embryonic Stem Cells," Nature Biotech. 19, (2001), pp. 1129-1133.
Zhou, J. et. al., "Induction of Tyrosine Hydroxylase Gene Expression in Human Foetal Cerebral Cortex," Neurosci. Lett. 252, (1998), pp. 215-217.
Li, M. "Generation of Purified Neural Precursors from Embryonic Stem Cells by Lineage Selection," Curr. Biol. 8, (1998), pp. 971-974.
Li, M. et. al., "Lineage Selection and Isolation of Neural Precursors from Embryonic Stem Cells," Symp. Soc. Exp. Biol. 53, (2001), pp. 29-42.
Lim, D. et. al., "Noggin Antagonizes BMP Signaling to Create a Niche for Adult Neurogenesis," Neuron 27, (2000), pp. 713-726.
Lim, J. et. al., "Proteosome Analysis of Conditioned Medium from Mouse Embryonic Fibroblast Feeder Layers which Support the Growth of Human Embryonic Stem Cells," Proteomics 2, (2002), pp. 1187-1203.
Ling, Z. et. al., Differentiation of Mesencephalic Progenitor Cells into Dopaminergic Neurons by Cytokines, Exp. Neurol. 149, (1998), pp. 411-423.
Liu, S. et. al., "Embryonic Stem Cells Differentiate into Oligodendrocytes and Myelinate in Culture and After Spinal Cord Transplantation," Proc. Natl. Acad. Sci. USA 97, (2000), pp. 6126-6131.
Lodish, H. (EDS.) et. al., "Molecular Cell Biology," 4th Edition, W. H. Freeman, New York, (2000), p. 968.
MacDonald, S. et. al., "A Population of Oligodendrocytes Derived from Multipotent Neural Precursor Cells Expresses a Cholinergic Phenotype in Culture and Responds to Ciliary Neurotrophic Factor," J. Neurosci. Res. 68, (2002), pp. 255-264.
Massague, J. "The TGF-Beta Family of Growth and Differentiation Factors," Cell 49, (1987), pp. 437-438.
Mayer-Proschel, M. et. al., "Isolation of Lineage-Restricted Neuronal Precursors from Multipotent Neuroepithelial Stem Cells," Neuron 19, (1997), pp. 773-785.
McDonald, J. et. al., "Transplanted Embryonic Stem Cells Survive, Differentiate and Promote Recovery in Injured Rat Spinal Cord," Nature Med. 5, (1999), pp. 1410-1412.
Mujtaba, T. et. al. "Lineage-Restricted Neural Precursors Can Be Isolated from Both the Mouse Neural Tube and Cultured ES Cells," Dev. Biol. 214, (1999), pp. 113-127.
Mummery, C. et. al., "Characteristics of Embryonic Stem Cell Differentiation: A Comparison with Two Embryonal Carcinoma Cell Lines," Cell Diff. Dev. 30, (1990), pp. 195-206.
Nih, "Stem Cells: Scientific Progress and Future Research Directions," Ch. 2, US Department of Health and Human Services, http://www.nih.gov/news/stemcell/scireport.htm, Jun. 17, 2001, pp. 5-10.

(56) References Cited

OTHER PUBLICATIONS

Nih, "Stem Cells: Scientific Progress and Future Research Directions," Executive Summary, Natl. Inst. Health, Jun. 17, 2001, 11 pp.
Odorico, J. et. al., "Multilineage Differentiation from Human Embryonic Stem Cell Lines," Stem Cells 19, (2001), pp. 193-204.
Okabe, S. et. al., "Development of Neural Precursor Cells and Functional Postmitotic Neurons from Embryonic Stem Cells In Vitro," Mech. Dev. 59, (1996), pp. 89-102.
O'Shea, K., "Embryonic Stem Cell Models of Development," Anatomical Record (New Anat.) 257(1), (1999), pp. 32-41.
Ostenfeld, T. et. al., "Human Neural Precursor Cells Express Low Levels of Telomerase In Vitro and Show Diminishing Cell Proliferation with Extensive Axonal Outgrowth Following Transplantation," Exp. Neurol. 164, (2000), pp. 215-226.
Pedersen, R., "Studies of In Vitro Differentiation with Embryonic Stem Cells," Reprod. Fertil. Dev. 6, (1994), pp. 543-552.
Piper, D. et. al., "Immunocytochemical and Physiological Characterization of a Population of Cultured Human Neural Precursors," J. Neurophysiol. 84(1), (2000), pp. 534-548.
Pleasure, S. et. al., "NTera 2 Cells: A Human Cell Line which Displays Characteristics Expected of a Human Committed Neuronal Progenitor Cell," J. Neurosci. Res. 35, (1993), pp. 585-602.
Pluchino, S. et. al., "Neural Stem Cells and Their Use as Therapeutic Tool in Neurological Disorders," Brain Res. Rev. 48, (2005), pp. 211-219.
Rao, M., "Multipotent and Restricted Precursors in the Central Nervous System," Anatomical Rec. (New Anatomist) 257, (1999), pp. 137-148.
Rathjen, J. et. al., "Formation of a Primitive Ectoderm Like Cell Population, EPL Cells, from ES Cells in Response to Biologically Derived Factors," J. Cell Sci. 112, (1999), pp. 601-612.
Rathjen, P. et. al., "Properties and Uses of Embryonic Stem Cells: Prospects for Application to Human Biology and Gene Therapy," Reprod. Fertil. Dev. 10, (1998), pp. 31-47.
Reubinoff, B. et. al., "Embryonic Stem Cell Lines from Human Blastocysts: Somatic Differentiation In Vitro," Nat. Biotech. 18, (2000), pp. 399-404.
Reubinoff, B. et. al., "Neural Progenitors from Human Embryonic Stem Cells," Nat. Biotech. 19, (2001), pp. 1134-1140.
Robertson, E., "Derivation and Maintenance of Embryonic Stem Cell Cultures," Meth. Mol. Biol. 75, (1997), pp. 173-184.
Rolletschek, A. et. al., "Differentiation of Embryonic Stem Cell-Derived Dopaminergic Neurons is Enhanced by Survival-Promoting Factors," Mech. Dev. 105, (2001), pp. 93-104.
Sasai, Y. et. al., "Regulation of Neural Induction by the Chd and Bmp-4 Antagonistic Patterning Signals in Zenopus," Nature 378—1 page errata, correcting original paper at Nature 376:333-6, (1995), p. 419.
Sato, N. et. al., "Molecular Signature of Human Embryonic Stem Cells and Its Comparison with the Mouse," Dev. Biol. 260, (2003), pp. 404-413.
Schuldiner, M. et. al., "Effects of Eight Growth Factors on the Differentiation of Cells Derived from Human Embryonic Stem Cells," Proc. Natl. Acad. Sci. USA 97(21), (2000), pp. 11307-11312.
Seaberg, R. et. al., "Neural Determination Genes Revealed by Expression Trapping in Embryonic Stem Cells," Soc. Neurosci. (29th Annual Meeting) 25:527 Abstract No. 205.17, (1999), p. 527.
Shamblott, M. et. al., "Derivation of Pluripotent Stem Cells from Cultured Human Primordial Germ Cells," Proc. Natl. Acad. Sci. USA 95, (1998), pp. 13726-13731.
Shingo, T. et. al., "Erythropoietin Regulates the In Vitro and In Vivo Production of Neuronal Progenitors by Mammalian Forebrain Neural Stem Cells," J. Neurosci. 21, (2001), pp. 9733-9743.
Smith, A., "Culture and Differentiation of Embryonic Stem Cells," J. Tiss. Cult. Meth. 13, (1991), pp. 89-94.
Smith, W., "TGF-Beta Inhibitors: New and Unexpected Requirements in Vertebrate Development," TiG 15(1), (1999), pp. 3-5.
Sorensen, T. et. al., "Safe Sorting of GFP-Transduced Live Cells for Subsequent Culture Using a Modified FACS Vantage," Cytometry 37, (1999), pp. 284-290.
Stagaard Janas, M. et. al., "Glial Cell Differentiation in Neuron-Free and Neuron-Rich Regions," Anat. Embryol. 184, (1991), pp. 559-569.
Storch, A. et. al., "Long-Term Proliferation and Dopaminergic Differentiation of Human Mesancephalic Neural Precursor Cells," Exp. Neurol. 170, (2001), pp. 317-325.
Strubing, C. et. al., "Differentiation of Pluripotent Embryonic Stem Cells into the Neuronal Lineage In Vitro Gives Rise to Mature Inhibitory and Excitatory Neurons," Mech. Dev. 53, (1995), pp. 275-287.
Studer, L. et. al., "Enhanced Proliferation, Survival, and Dopaminergic Differentiation of CNS Precursors in Lowered Oxygen," J. Neurosci. 20, (2000), pp. 7377-7383.
Thompson, S. et. al., "Cloned Human Teratoma Cells Differentiate into Neuron-Like Cells and Other Cell Types in Retinoic Acid," J. Cell Sci. 72, (1984), pp. 37-64.
Thomson, J. et. al., "Embryonic Stem Cell Lines Derived from Human Blastocysts," Science 282, (1998), pp. 1145-1147.
Thomson, J. et. al., "Isolation of a Primate Embryonic Stem Cell Line," Proc. Natl. Acad. Sci. USA 92, (1995), pp. 7844-7848.
Thomson, J. et. al., "Neural Differentiation of Rhesus Embryonic Stem Cells," APMIS 106, (1998), pp. 149-156.
Trojanowski, J. et. al., "Transfectable and Transplantable Postmitotic Human Neurons: A Potential 'Platform' for Gene Therapy of Nervous System Diseases," Exp. Neurol. 144, (1997), pp. 92-97.
Tropepe, V. et. al., "Autonomous Neural Cell Fate Specification in Mouse Embryonic Stem Cells," Soc. Neurosci. 25, Abstract No. 205.18, (1999), p. 527.
Tropepe, V. et. al., "Neural Determination Genes Revealed by Expression Trapping in Embryonic Stem Cells," Soc. Neurosci. 25, Abstract No. 205.17, (1999), p. 527.

\* cited by examiner

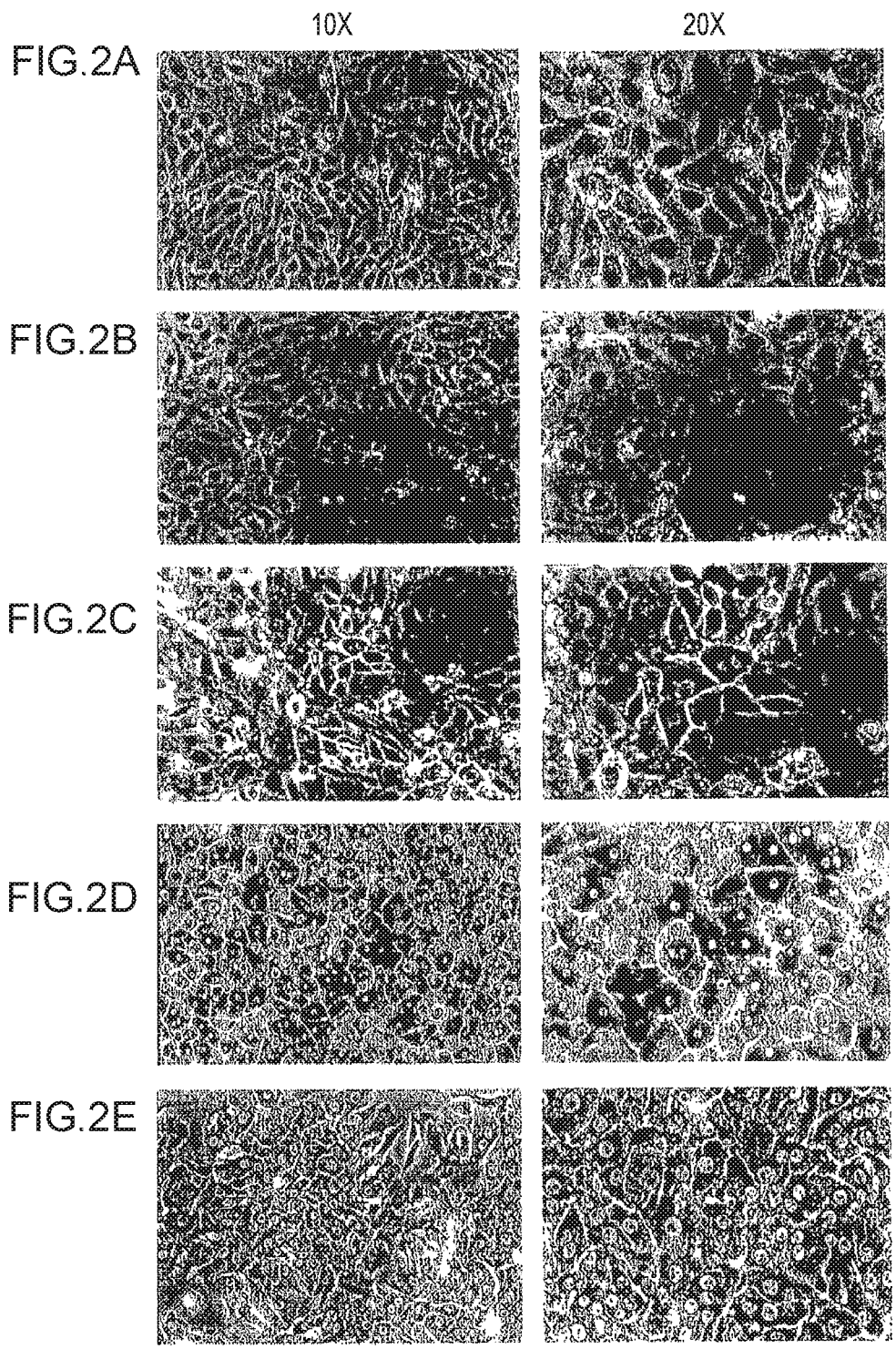

| Gene | 2 | 4 | 8 | 4-/4+ |
|---|---|---|---|---|
| Asparagine synthetase | 1.3 | 2.8 | 2 | 1.5 |
| ATL-derived PMA-responsive (APR peptide) | 1.6 | 3.6 | 2.4 | |
| CD9 antigen | 1.9 | 4.6 | 3.7 | 1.1 |
| Protein Translation Factor SUI1 homolog | 2.5 | 1.7 | 1.9 | 2.2 |
| Thrombospondin 1 | 3.7 | 2.9 | 3.1 | 2.8 |
| Connective tissue growth factor | 2.6 | 2.2 | 2.2 | 1.8 |
| Tropomyosin alpha chain | 2.5 | 2.4 | 2.1 | 2.4 |
| Myeloid cell leukemia sequence 1 | 2.4 | 2.2 | 2.4 | 2.8 |
| E-MAP-115 | 2.1 | 2 | 2.7 | 2 |
| TGF-beta inducible early protein (TIEG) | 2.6 | 1.6 | | 1.5 |
| EST w.s.t.deoxyribose-phosphate aldolase | 1.4 | 2.5 | 1.6 | 1.8 |
| EST (IMAGE:70082) | 1.5 | 2.5 | 1.7 | 1.9 |
| Collagen, type IV, alpha 2 | 2.6 | 2 | | |
| EST (IMAGE:113634) | 2.2 | 2.2 | 2.9 | 1.9 |
| Ubiquitin-conjugating enzyme E2A (RAD6 homolog) | 2 | 1.8 | 2.6 | 2.3 |
| t factor (complement) | 1.6 | 1.4 | 2.6 | 1.3 |
| E-Map-115 mRNA | 1.8 | 1.7 | 2.8 | 1.6 |
| EST (IMAGE:293446) | 1.6 | 1.5 | 2.6 | 1.7 |
| EST (IMAGE:134862) | 1.6 | 1.4 | 2.9 | 1.8 |
| EST h.s.t. phosphotyrosine independent ligand p628 | 1.5 | 1.8 | 3.1 | 2.5 |
| EST m.s.t. ENV Polyprotein | 1.5 | 1.9 | 3.1 | 2.7 |
| Threonyl-tRNA synthetase | 1.7 | 1.6 | 3.4 | 2.8 |
| Human protocadherin 42 | 1.9 | 1.7 | 2.6 | 3.1 |
| EST h.s.t. Phosphoserine Aminotransferase | 2.1 | 1.9 | 2.3 | 2.5 |
| connexin 32 | 2 | 2 | 3.1 | 3.3 |
| metallothionein from cadmium-treated cells | 3.1 | 2.1 | 3.3 | 3.6 |

Continued on Fig.3B

| Gene | 2 | 4 | 8 | 4-/4+ |
|---|---|---|---|---|
| Cadherin 2, N-cadherin | -2 | -2.5 | -1.7 | -1.6 |
| CAGH3 | -2 | -2.5 | -1.2 | -1.2 |
| Apolipoprotein B | -2.5 | -3 | -1.6 | -1.9 |
| Plasminogen activator, urokinase receptor | -2.6 | -2.3 | -2 | -1.6 |
| neuronal pentraxin 1 (NPTX1) | -2.9 | -2.5 | -2.2 | -1.5 |
| EST (IMAGE:357800) | -2.7 | -2.3 | -2.1 | -1.4 |
| nuclear orphan receptor LXR-alpha | -2.6 | -2.2 | -2.1 | -1.2 |
| Apolipoprotein B | -2.3 | -2 | -2.8 | -1.7 |
| Cyclin D2 | -3.9 | -2.9 | -2.9 | -1.3 |
| nucleotide-binding protein | -3.1 | -2.2 | -2 | -1.5 |
| 5'-AMP-activated protein kinase, gamma-1 subunit | -3.6 | -2.9 | -3.1 | -1.9 |
| Fibronectin 1 | -4.2 | -3.4 | -3.3 | -1.8 |
| Fibrinogen, A alpha polypeptide | -2.8 | -3.4 | -4.1 | -2.7 |
| Fibrinogen beta chain | -2 | -2.1 | -2.9 | -2.7 |
| EST (Image: 487537) | -2.5 | -2.5 | -2.5 | -2.5 |
| Homeo box B5 (2.1 protein) | -2 | -2.2 | -2.7 | -2.8 |
| EST (IMAGE:358836) | -2 | -2.9 | -7.2 | -3.5 |
| Plasma retinol-binding protein | -2.7 | -3.1 | -5.3 | -2.8 |
| alpha-1-antitrypsin | -2.2 | -3.2 | -7.7 | -3.5 |
| Apolipoprotein A-1 | -5.4 | -5.4 | -6.7 | -3.5 |
| Apolipoprotein A-1 | -5.2 | -4.6 | -4.1 | -3.5 |
| Alpha-fetoprotein | -7.5 | -15.8 | -22.1 | -22.9 |
| Alpha-fetoprotein | -8.6 | -22.1 | -28 | -25.9 |
| EST (IMAGE:230528) | -1.7 | -3.1 | -15.1 | -12.5 |
| cAMP-specific phosphodiesterase 8A (PDE8A) | -1.2 | -1.5 | -6.2 | -5.9 |
| APOLIPOPROTEIN AI REGULATORY PROTEIN-1 | -1.2 | -1.6 | -5.7 | -6.2 |

FIG.3A

| Continued from Fig.3A | | | | | | | |
|---|---|---|---|---|---|---|---|
| Human metallothionein (MT)-I-F-gene | 2.2 | 1.6 | 2.4 | 2.5 | EST(IMAGE:346531) | 1.1 | -3.7 | -4.5 |
| EST(IMAGE:241398) | 1.2 | 2.5 | 1.8 | 2.2 | EST(IMAGE:301416) | | -1.3 | -3.2 | -4 |
| EST(IMAGE:51718) | 1.7 | 2.7 | 1.9 | 2.3 | go130, oncostatin M receptor | 1 | -1.3 | -3.2 | -4.1 |
| KIAA0278 gene | 1.5 | 3 | 2.5 | 2.7 | EST(IMAGE:286521) | -1.3 | -1.9 | -3.2 | -2 |
| EST w.s.t.thymidine diphosphoglucose 4,6-dehydratase | 1.6 | 3 | 2.2 | 2.7 | KIAA0287 gene | -1.3 | -1.8 | -3.7 | -3.7 |
| EST(IMAGE:48196) | 1.6 | 3.2 | 2.5 | 2.3 | Ini1 | -1.2 | -1.5 | -3.7 | -2.2 |
| EST(IMAGE:247574) | 1.4 | 3.7 | 2.5 | 2.7 | excitatory amino acid transporter 4 mRNA | -1.4 | -1.5 | -2.3 | -2.9 |
| Fibroblast growth factor 9 (glia-activating factor) | 1.5 | 3.6 | 2.6 | 2.6 | EST(IMAGE:151339) | -1.2 | -1.3 | -2 | -2.5 |
| EST(IMAGE:200696) | 2.2 | 3.2 | 2.7 | 2.9 | guanine nucleotide exchange factor mss4 | 1.9 | | -2.5 | -2.3 |
| EST(IMAGE:235092) | 1.6 | 3.1 | 3.2 | 2.7 | EST h.s.t. TIP120 | 1.1 | -1.2 | -2.6 | -2.3 |
| EST(IMAGE:356631) | 2.6 | 3.2 | 3.1 | 2.6 | EST(IMAGE:128990) | -1.3 | -1.5 | -2.2 | -2.7 |
| EST(IMAGE:276915) | 1.4 | 1.9 | 7.9 | 6 | EST(IMAGE:347761) | | | | -3.3 |
| EST(IMAGE:41364) | 1.2 | 2.2 | 6.1 | 5.1 | EST(IMAGE:166622) | -1.7 | -1.9 | -1.8 | -2.6 |
| secreted frizzled related protein | 1.7 | 1.6 | 3.8 | 4.7 | EST(IMAGE:180082) | -1.4 | -1.5 | -2.8 | -2.1 |
| EST(IMAGE:361415) | 1.2 | 2.8 | 4 | 6.3 | EST(IMAGE:151231) | -1.6 | -1.5 | -2.6 | -2 |
| EST(IMAGE:260067) | 1.7 | 2.3 | 4.4 | 3.8 | DESMOPLAKIN I AND II | -1.7 | -1.6 | -2.8 | -2.2 |
| EST(IMAGE:293567) | 1.8 | 3.6 | 5 | 4.2 | EST(IMAGE:487428) | -1.2 | -1.3 | -2.5 | -2 |
| uridine diphosphoglucose pyrophosphorylase | 2 | 2.6 | 6.5 | 7.1 | EST(IMAGE:48537) | -1.3 | -1.5 | -2.5 | -2.2 |
| EST w.s.t. Homeobox protein OTX2 | 2 | 2.5 | 5.3 | 5.7 | EST h.s.t. Citrate synthase | -1.6 | -1.8 | -2.8 | -2.4 |
| Vinculin | 2.2 | 2.6 | 4.1 | 5 | EST(IMAGE:46928) | -1.6 | -1.6 | -2.5 | -2.4 |
| Human metallothionein-Ie gene (hMT-Ie) | 2.8 | 2.2 | 3.4 | 4.3 | EST(IMAGE:429017) | -1.3 | -1.6 | -2.6 | -2.1 |
| Cyr61 | 2.9 | 3.1 | 4.5 | 4.9 | KIAA0059 gene | -1.1 | -1.2 | -2.7 | -2.3 |
| EST(IMAGE:380214) | 1.9 | 3.5 | 11.5 | 9.5 | EST(IMAGE:381780) | -1.2 | -1.2 | -2.7 | -2.4 |
| Procollagen-proline, 2-oxoglutarate 4-dioxygenase | 1.8 | 4.1 | 20.8 | 16.7 | EST(IMAGE:242643) | -1.2 | -1.4 | -2.7 | -2.5 |
| Phosphoglucomutase 1 | 1.4 | 3 | 9.7 | 12.4 | Erythroid alpha-spectrin | -1.1 | -1.4 | -2.8 | -2.4 |
| EST(IMAGE:380190) | 1.2 | 3.1 | 12.6 | 17.4 | EST h.s.t. AQUAPORIN 3 | -1.2 | -1.3 | -2.6 | -2.6 |
| EST(IMAGE:380301) | 1.5 | 4.1 | 3.1 | 3.4 | MAP kinase | -1.5 | -1.7 | -3 | -2.5 |

FIG. 3B

TREATMENT B
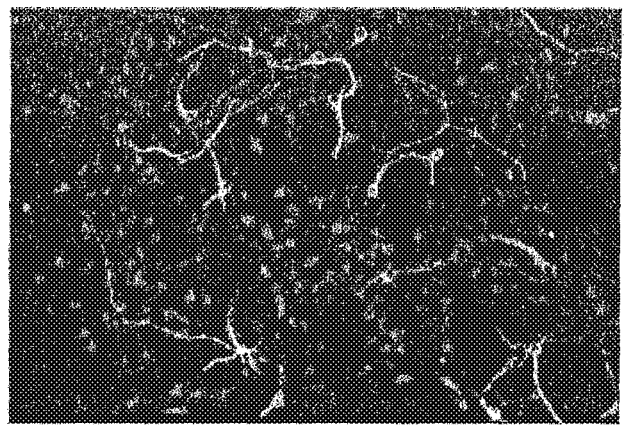
TREATMENT D
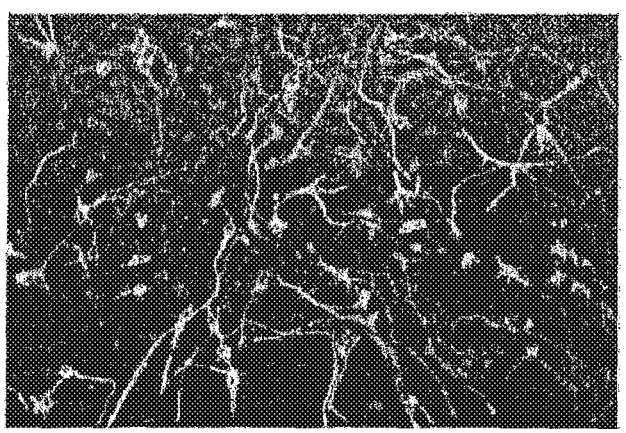
TREATMENT F
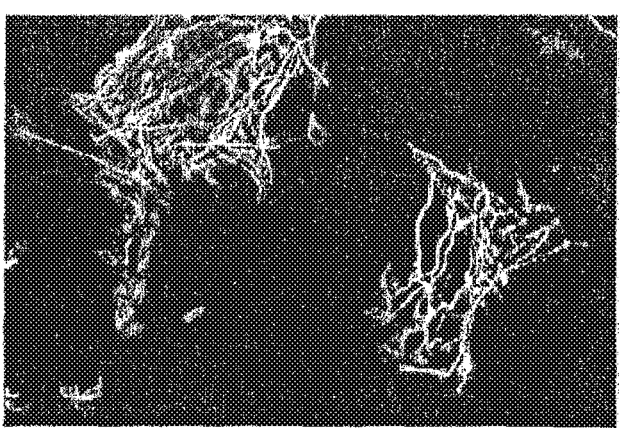
FIG.4

NEURAL CELL POPULATIONS FROM PRIMATE PLURIPOTENT STEM CELLS

RELATED APPLICATIONS

This application is a divisional of pending U.S. utility application Ser. No. 09/888,309, filed Jun. 21, 2001, through which it claims priority to the following U.S. provisional patent applications: U.S. Ser. No. 60/213,740, filed Jun. 22, 2000; U.S. Ser. No. 60/213,739, filed Jun. 22, 2000; U.S. Ser. No. 60/216,387, filed Jul. 7, 2000; and U.S. Ser. No. 60/220,064, filed Jul. 21, 2000. This application is also a continuation-in-part of U.S. Ser. No. 10/873,414, filed Jun. 21, 2004.

The following patent applications are hereby incorporated herein by reference in their entirety: U.S. Ser. No. 09/888,309, filed Jun. 21, 2001; U.S. Ser. No. 60/213,740, filed Jun. 22, 2000; U.S. Ser. No. 60/213,739, filed Jun. 22, 2000; U.S. Ser. No. 60/216,387, filed Jul. 7, 2000; U.S. Ser. No. 60/220,064, filed Jul. 21, 2000; U.S. Ser. No. 60/175,581, filed Jan. 11, 2000; U.S. Ser. No. 09/688,031, filed Oct. 10, 2000; U.S. Ser. No. 09/718,308, filed Nov. 20, 2000, U.S. Ser. No. 60/257,608, filed Dec. 22, 2000; International Patent Application PCT/US01/01030, filed Jan. 10, 2001; International Patent Application PCT/US01/13471, filed Apr. 26, 2001; and U.S. Ser. No. 09/859,351, filed May 16, 2001.

TECHNICAL FIELD

This invention relates generally to the field of cell biology of embryonic cells. More specifically, it relates to conditions that allow human pluripotent stem cells to be directly differentiated into cells of a particular lineage, suitable for applications such as use in tissue regeneration and the screening of biologically active substances.

BACKGROUND

Recent discoveries have raised expectations that stem cells may be a source of replacement cells and tissues that are damaged in the course of disease, infection, or because of congenital abnormalities. Various types of putative stem cells differentiate when they divide, maturing into cells that can carry out the unique functions of particular tissues, such as the heart, the liver, or the brain.

A particularly important discovery has been the development of pluripotent stem cells, which are thought to have the potential to differentiate into almost any cell type. The next challenge in developing the technology is to obtain dependable conditions for driving differentiation towards particular cell lineages that are desired for therapeutic purposes.

Early work on embryonic stem cells was done in mice (reviewed in Robertson, Meth. Cell Biol. 75:173, 1997; and Pedersen, Reprod. Fertil. Dev. 6:543, 1994). Most methods of differentiating mouse pluripotent stem cells involve three strategies, often in combination:

- Permitting the cells to form aggregates or embryoid bodies, in which cells interact and begin to differentiate into a heterogeneous cell population with characteristics of endoderm, mesoderm, and ectoderm cells. The embryoid bodies are then harvested and cultured further so that the differentiation can continue.
- Inducing the cells to differentiate using soluble factors that promote particular forms of differentiation, optionally with simultaneous withdrawal of factors that inhibit differentiation
- Transfecting the cells with a tissue-specific gene, that has the effect of directing the cell towards the tissue type desired Mummery et al. (Cell Differentiation Dev. 30:195, 1990) compared characteristics of mouse embryonic stem (ES) cells with two embryonal carcinoma lines. The cells were differentiated either by letting cells form aggregates, optionally in the presence of retinoic acid (RA) or dimethyl sulfoxide (DMSO); or letting the cells grow to confluence, optionally depriving the culture of leukemia inhibiting factor (LIF) or differentiation inhibiting activity (DIA) found in high concentrations in medium conditioned by Buffalo rat liver (BRL) cells. The study suggested that mixed endoderm-mesoderm cells were obtained after removing inhibitors of differentiation, and parietal endoderm-like cells were obtained by RA induction.

Grendon et al. (Dev. Biol. 177:332, 1996) generated an endothelial cell line capable of embryonic vasculogenesis from mouse ES cells. The cells were transfected with the early region of SV40 Large T antigen, and then cultured in medium comprising homogenized mouse testes, which promotes differentiation. An endothelial line was derived that expresses endothelial cell specific proteins and can be induced by basic fibroblast growth factor (bFGF) and LIF to proliferate to form vascular tubes and microcapillary anastomoses.

Van Inzen et al. (Biochim. Biophys. Acta 1312:21, 1996) differentiated mouse embryonic stem cells by incubating the cells for at least 3 days with retinoic acid. The cells were cultured either as a monolayer, or as embryoid bodies on a non-adhesive substrate. The cells obtained from culture stained positively for the neuronal markers NF-165 and GAP-43, and were electrically excitable in a patch clamp assay.

Dinsmore et al. (Cell Transplant. 5:131, 1996) report a method for controlled differentiation of mouse embryonic stem cells in vitro to produce populations containing neurons or skeletal muscle cells. Embryoid bodies were allowed to form, and were induced using dimethyl sulfoxide (DMSO) to differentiate to muscle cells, or using retinoic acid to differentiate to neurons. Muscle cells were also made by transfecting ES cells with an expression vector for muscle-specific protein MyoD.

Rathjen et al. (J. Cell Sci. 112:601, 1999, and International Patent Publication WO 99/53021) formed a primitive ectoderm-like (EPL) cell population from mouse ES cells using conditioned medium from the human hepatocarcinoma line HepG2. When grown in medium without feeder cells, but including LIF, the mouse ES cells reportedly grew as a homogeneous population with most colonies displaying domed morphology. Differentiation was effected by culturing the mouse ES cells in the presence of LIF and HepG2 conditioned medium. This gave rise to a morphologically distinct population of EPL cells with different phenotypic markers and altered differentiation properties. EPL cell formation was reversible in the presence of LIF by withdrawing the conditioned medium.

Tropepe et al. (Soc. Neuroscience 25: abstract 205.18, 1999) reported that a small percentage of mouse ES cells proliferate in serum-free low-density conditions in the presence of LIF, and form sphere colonies that may subsequently differentiate into neurons and glia. A small proportion of cells from primary colonies can generate secondary colonies independent of LIF but dependent on the factor FGF2. Blocking BMP signaling by adding noggin protein increases the proportion of cells forming neural stem cells. About 60% of single ES cells cultured for 24 h in serum-free medium express nestin.

Pluripotent Stem Cells of Human Origin

Work on human pluripotent stem (hPS) cells has been more than a decade behind the experiments conducted on mouse cells. Human PS cells are more fragile and more difficult to isolate. Furthermore, they cannot be maintained in an undifferentiated state under conditions developed for mouse cells.

Recently, some of these challenges have been overcome. Thomson et al. (U.S. Pat. No. 5,843,780; Proc. Natl. Acad. Sci. USA 92:7844, 1995) were the first to successfully culture stem cells from non-human primates. Thomson et al. also derived human embryonic stem (hES) cell lines from human blastocysts (Science 282:114, 1998). Gearhart and coworkers derived human embryonic germ (hEG) cell lines from fetal gonadal tissue (Shamblott et al., Proc. Natl. Acad. Sci. USA 95:13726, 1998 and International Patent Publication No. WO 98/43679). Both hES and hEG cells have the long-sought characteristics of hPS cells: they are capable of long-term proliferation in vitro without differentiating, they retain a normal karyotype, and they retain the capacity to differentiate to a number of different derivatives.

Human pluripotent stem cells differ from mouse ES cells in a number of important respects. Thomson et al. and Gearhart et al. maintained their hPS cells in an undifferentiated state by culturing on a layer of embryonic feeder cells. In contrast, mouse ES cells can be grown easily without feeder cells in appropriate conditions, particularly the presence of leukemia inhibiting factor (LIF) or other ligands that bind receptors that associate with gp130. However, LIF alone has not been reported to prevent differentiation of hPS in the absence of feeders. Another difference is that mouse ES cells can be plated in a completely dispersed fashion; and grow quite happily to produce undifferentiated ES progeny. In contrast, single hES cells are unstable; and propagation of hES cells typically requires that they be passaged as clusters of cells during each replating.

Current efforts to differentiate hPS cells involve the formation of cell aggregates, either by overgrowth of hPS cells cultured on feeders, or by forming embryoid bodies in suspension culture. The embryoid bodies generate cell populations with a highly heterogeneous mixture of phenotypes, representing a spectrum of different cell lineages—which depends in part on the size of each aggregate and the culture conditions.

Large-scale commercial production of committed precursor cells or fully differentiated cells from hPS cells would require a differentiation protocol that did not involve producing cell aggregates or embryoid bodies. In addition, there is a need for cell populations that have relatively uniform and reproducible characteristics for use in drug screening and human therapy.

Accordingly, there is a need for new technology that facilitates derivation of differentiated cells from human pluripotent stem cells.

SUMMARY

This invention provides a system for efficient production of differentiated cells from primate pluripotent stem (pPS) cells. Rather than permitting the pPS to form embryoid bodies, differentiation is effected directly by plating subconfluent cultures of pPS cells onto a solid surface that facilitates differentiation, in the absence of feeder cells or culture conditions that simulate the presence of feeder cells. The nature of the solid surface and components of the culture medium can be chosen to direct differentiation down a cell lineage pathway that is desired for research or therapeutic use.

Embodied in this invention are methods for directly obtaining differentiated cells from a donor culture of undifferentiated pPS cells, without forming embryoid bodies. Undifferentiated cells are newly plated onto a solid surface, or otherwise exchanged into a new culture environment that induces differentiation of the cells into the desired phenotype in a direct fashion, without overgrowth, aggregate formation, or otherwise creating the condensed heterogeneous cell population characteristic of embryoid bodies.

One way of accomplishing this is to prepare a suspension of cells from an undifferentiated donor culture; replate and culture the suspended cells on a solid surface so that they differentiate without forming embryoid bodies; and harvest differentiated cells from the solid surface. A variation is to harvest pPS cells from the donor culture before there is overgrowth or formation of colonies; replate and culture the harvested cells on a solid surface so that they differentiate; and harvest differentiated cells from the solid surface. Another variation is to prepare a suspension from a culture of both pPS cells and feeder cells; replate and culture the suspended cells on a solid surface without adding fresh feeder cells; and harvest differentiated cells from the solid surface. A further variation is to provide a donor culture comprising undifferentiated pPS cells growing on an extracellular matrix in the absence of feeder cells; prepare a suspension of cells from the donor culture; replate and culture the suspended cells on a solid surface without the extracellular matrix; and harvest differentiated cells from the solid surface.

A further variation is to provide a culture of primate pluripotent stem (pPS) cells that is essentially free of feeder cells; change the medium in which the cells are cultured; and harvest differentiated cells from the culture after culture for a sufficient period to effect differentiation in the changed medium. The medium may be changed either by replacing the medium in the culture with a fresh medium having a new composition, or by adding new constituents to the medium already present and then continuing the culture.

In any of these embodiments, the pPS cells are any type of cell capable of forming progeny of each of the three germ layers, exemplified but not limited to human embryonic stem (hES) cells. The replating can be performed without selecting a particular cell population from the suspended (or harvested) cells. For example, the replated cell suspension can be obtained by incubating the donor culture with collagenase or trypsin or E.D.T.A., thereby releasing the cells from a surface to which the cells adhere, and collecting the released cells in a suitable medium. The replating can be done in the absence of freshly added feeder cells or extracellular matrix proteins on the solid surface, such as a glass cover slip, optionally bearing a polycation such as polyornithine or polylysine.

Differentiation can be promoted by withdrawing serum or serum replacement from medium, withdrawing a factor that promotes proliferation, withdrawing a factor that inhibits differentiation, or adding a new factor that promotes differentiation. Exemplary factors for generating neuronal cells are Brain Derived Neurotrophic Factor (BDNF) and Neutrotrophin-3 (NT-3).

A proportion of the cells cultured according to this invention may differentiate to precursor cells committed to a restricted cell lineage and capable of proliferation, such as ectodermal cells (for example, neuroectoderm lineage), mesodermal cells, or cells of the endoderm or visceral endoderm. A proportion of the cells may become fully differentiated cells, such as neurons or glial cells. If desired, the harvested committed precursor cells or fully differentiated cells can optionally be genetically altered with a polynucleotide that encodes telomerase.

The differentiated cells of this invention may be used to screen candidate compounds or environmental conditions that affect differentiation or metabolism of a cell type of interest. The differentiated cells may be used to obtain cell specific antibody preparations and cell-specific cDNA libraries, to study patterns of gene expression, or as an active ingredient in a pharmaceutical preparation.

The differentiated cells of this invention can also be used to identify a substance expressed at a different level in committed or differentiated cells compared with undifferentiated primate pluripotent stem (pPS) cells. Such substances may include but are not limited to mRNA transcripts, secreted protein, intracellular protein, cell-surface protein, cell-surface oligosaccharide, and particular lipids or gangliosides. Expression may be compared, for example, at the level of transcription, translation, surface presentation, or enzymatic activity. Expression of oligosaccharide and lipid substances can be inferred by chemical or antibody analysis, or by deduction from expression of enzymes required for their synthesis. Particular embodiments involve determining the level of expression of a plurality of mRNAs in committed or differentiated cells made by direct differentiation, embryoid body formation, or any other suitable technique, and comparing the level determined with the level of expression of the same mRNAs in another cell type, such as undifferentiated pPS cells. A polynucleotide can then be prepared that shares sequence with mRNA that is expressed at a different level in the differentiated cells.

These and other embodiments of the invention will be apparent from the description that follows.

DRAWINGS

FIG. 1 provides an analysis of OCT-4 and hTERT expression in hES cells cultured with feeder cells (mEF) or extracellular matrix (Matrigel® or laminin) with regular medium (RM) or conditioned medium (CM). The upper panel is a copy of a gel showing OCT-4 and hTERT expression at the mRNA level by RT-PCR. The lower panel is a bar graph comparing the level of expression for cells grown on different substrates, expressed as the ratio of OCT-4 or hTERT to the 18s standard. hES cells grown on Laminin and Matrigel® in conditioned medium have similar expression patterns to those of cells grown on a feeder layer.

FIGS. 2A-2E are half-tone reproductions of phase contrast photomicrographs (10×, 40×), showing cells at various times during direct differentiation to a hepatocyte phenotype. FIG. 2A shows cells 4 days after culture in SR medium containing 5 mM sodium N-butyrate. More than 80% of cells in the culture are large in diameter, containing large nuclei and granular cytoplasm. After 5 days, the cells were switched to specialized hepatocyte culture medium (HCM). FIG. 2B and FIG. 2C show the appearance after culturing in HCM for 2 or 4 days. Multinucleated polygonal cells are common. By these criteria, the directly differentiated ES-derived cells resemble freshly isolated human adult hepatocytes (FIG. 2D) and fetal hepatocytes (FIG. 2E).

FIG. 3A and FIG. 3B are a matrix chart, representing relative expression of mRNA in embryoid body (EB) cells, compared with expression in the undifferentiated hES cell line from which they were derived. Probes used to analyze expression are listed to the left. The first three columns of the matrix show the kinetics of relative expression for EB cells cultured for 2, 4, or 8 days. The fourth column (4 d−/4 d+) shows relative expression of EB cells to which retinoic acid was added for the final 4 days of culture.

FIG. 4 is a reproduction of a fluorescence micrograph, showing neuronal cell obtained by direct differentiation of ES cells on a solid substrate using a mixture of differentiation factors. The three fields shown were all taken from treatments that comprised neurotrophins and the TNF-β superfamily antagonists noggin and follistatin. A number of cells are seen that have neuronal processes and stain for the neuronal marker β-tubulin III. The proportion of MAP-2 positive cells that were also positive for tyrosine hydroxylase (a marker for dopaminergic neurons) was as high as ~15%.

DETAILED DESCRIPTION

This invention provides a system for directly differentiating primate pluripotent stem (pPS) cells into committed precursor cells or fully differentiated cells. The system avoids forming aggregates or embryoid bodies as an intermediate step. hPS cells are maintained as a monolayer or dispersed from a sub-confluent pPS culture, and plated onto a suitable substrate in an appropriate culture environment that promotes differentiation.

Before this invention was made, the expectation was that a strategy avoiding embryoid bodies would be unsuccessful. Classical developmental biology suggests that interaction between the three germinal layers of the embryo is essential for appropriate differentiation. Embryoid bodies are reminiscent of this early stage of development, in that they form the three germ layers in juxtaposition.

For example, nervous tissue is formed from the ectoderm. Recent evidence from the expression patterns of a number of genes suggests that another germ layer—the primitive endoderm—is involved in specifying neural fate in the mouse (Bouwmeester et al., BioEssays 19:855, 1997; reviewed in Davidson et al., "Cell lineage and Fate Determination", Academic Press, 1999; pp. 491-504 at 498). Endoderm ablation experiments strongly implicate an interaction of two germ layers that successively express the Hesx1 gene during gestation—which raises the possibility that such interactions may be critical for the specification of neural fate of the epiblast. Chimeric embryos deficient in the nodal gene fail to develop forebrain (Varlet et al., Development 124:1033, 1997). Results of nodal and hex1 studies strongly suggest that there is a critical requirement for the specification of neural cells in the epiblast. In addition, isolated epiblast from early embryos is unable to express brain specific genes Otx2, En1, and En2 unless they are cultured together with fragments of the mesoendoderm. This evidence suggests that cells from all three germ layers participate in neural differentiation in the epiblast.

Cells from all three germ layers are present in embryoid bodies, and provide an amalgam of signaling that may be similar to signaling that occurs during normal embryo development. But this type of interaction between different cell types is lacking when pPS cells are plated in monolayers.

Contrary to previous expectations, it has now been discovered that plating undifferentiated hES cells directly onto a suitable surface or changing medium in monolayer culture provides a system whereby a differentiated cell population may be reliably derived—in spite of the signaling one might expect to be lacking from cells of other germ layers.

In an exemplary experiment, cultures of rhesus and human ES lines grown on feeder cells were harvested using collagenase, and the cells were then dissociated to clusters of ~50-100 cells. The cells were then plated onto glass coverslips coated with poly-ornithine, and cultured for 1 week. Cultures showed positive immunoreactivity for β-tubulin III and MAP-2, markers that are characteristic of neurons; glial fibrillary acidic protein (GFAP), which is characteristic of astrocytes; and GalC, which is characteristic of oligodendrocytes—indicating that all three major cell phenotypes of the central nervous system were present.

Under optimized conditions, this system can provide a remarkably consistent population of differentiated cells, with less heterogeneity than what is present in a population of embryoid-body derived cells. Example 5 of this disclosure illustrates that the direct differentiation method can be used to obtain populations that are highly enriched for dopaminergic neurons. The direct differentiation method provides an important source of reproducible high-quality cells for use in therapy and drug screening.

Definitions

Prototype "primate Pluripotent Stem cells" (pPS cells) are pluripotent cells derived from pre-embryonic, embryonic, or fetal tissue at any time after fertilization, and have the characteristic of being capable under the right conditions of producing progeny of several different cell types. pPS cells are capable of producing progeny that are derivatives of each of the three germinal layers: endoderm, mesoderm, and ectoderm, according to a standard art-accepted test, such as the ability to form a teratoma in a suitable host.

Included in the definition of pPS cells are embryonic cells of various types, exemplified by human embryonic stem (hES) cells, as described by Thomson et al. (Science 282:1145, 1998); embryonic stem cells from other primates, such as Rhesus or marmoset stem cells described by Thomson et al. (Proc. Natl. Acad. Sci. USA 92:7844, 1995; Developmental Biology 38:133, 1998); and human embryonic germ (hEG) cells, described in Shamblott et al. (Proc. Natl. Acad. Sci. USA 95:13726, 1998). Other types of pluripotent cells are also included in the term. Any cells of primate origin that are capable of producing progeny that are derivatives of all three germinal layers are included, regardless of whether they were derived from embryonic tissue, fetal tissue, or other sources. For many embodiments of the invention, it is beneficial to use pPS cells that are karyotypically normal and not derived from a malignant source.

pPS cell cultures are described as "undifferentiated" or "substantially undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view with high nuclear/cytoplasmic ratios and prominent nucleoli. It is understood that colonies of undifferentiated cells within the population will often be surrounded by neighboring cells that are differentiated. Nevertheless, the undifferentiated colonies persist when the population is cultured or passaged under appropriate conditions, and individual undifferentiated cells constitute a substantial proportion of the cell population. Cultures that are substantially undifferentiated contain at least 20% undifferentiated pPS cells, and may contain at least 40%, 60%, or 80% in order of increasing preference (in terms percentage of cells with the same genotype that are undifferentiated). Using the methods described in this disclosure, it is sometimes possible to develop or passage cultures that contain a relatively low proportion of differentiated pPS cells (even as low as 5 or 10%) into cultures that are substantially undifferentiated.

Whenever a culture or cell population is referred to in this disclosure as proliferating "without differentiation", what is meant is that after proliferation, the composition is substantially undifferentiated according to the preceding definition. Populations that proliferate through at least four passages (~20 doublings) without differentiation will contain substantially the same proportion of undifferentiated cells (or possibly a higher proportion of undifferentiated cells) when evaluated at the same degree of confluence as the originating culture.

"Feeder cells" or "feeders" are cells of one type that are co-cultured with cells of another type, to provide an environment in which the cells of the second type can grow. The feeder cells are optionally from a different species as the cells they are supporting. For example, certain types of pPS cells can be supported by primary cultures of mouse embryonic fibroblasts, immortalized mouse embryonic fibroblasts, or human fibroblast-like cells differentiated from hES cells, as described later in this disclosure. In coculture with pPS cells, feeder cells are typically inactivated by irradiation or treatment with an anti-mitotic agent such as mitomycin c, to prevent them from outgrowing the cells they are supporting. For use in producing conditioned medium, inactivation of the cells may be optional, and depends in part on mechanical aspects of medium production.

pPS cell populations are said to be "essentially free" of feeder cells if the cells have been grown through at least one round after splitting in which fresh feeder cells are not added to support the growth of the pPS. It is recognized that if a previous culture containing feeder cells is used as a source of pPS for the culture to which fresh feeders are not added, there will be some feeder cells that survive the passage. For example, hES cells are often cultured in a 9.6 cm$^2$ well on a surface of ~375,000 primary irradiated embryonic fibroblasts near confluence. By the end of the culture, perhaps 150,000 feeder cells are still viable, and will be split and passaged along with hES that have proliferated to a number of ~1 to 1.5 million. After a 1:6 split, the hES cells generally resume proliferation, but the fibroblasts will not grow and only a small proportion will be viable by the end of ~6 days of culture. This culture is essentially free of feeder cells, with compositions containing less than about 5% feeder cells. Compositions containing less than 1%, 0.2%, 0.05%, or 0.01% feeder cells (expressed as % of total cells in the culture) are increasingly more preferred.

Whenever a culture or cell population is referred to in this disclosure as "feeder-free", what is meant is that the composition is essentially free of feeder cells according to the preceding definition, subject only to further constraints if explicitly required.

A "growth environment" is an environment in which cells of interest will proliferate or differentiate in vitro. Features of the environment include the medium in which the cells are cultured, the temperature, the partial pressure of $O_2$ and $CO_2$, and a supporting structure (such as a substrate on a solid surface) if present.

A "nutrient medium" is a medium for culturing cells containing nutrients that promote proliferation. The nutrient medium may contain any of the following in an appropriate combination: isotonic saline, buffer, amino acids, antibiotics, serum or serum replacement, and exogenously added factors. A "conditioned medium" is prepared by culturing a first population of cells in a medium, and then harvesting the medium. The conditioned medium (along with anything secreted into the medium by the cells) may then be used to support the growth of a second population of cells.

"Embryoid bodies" is a term of art synonymous with "aggregate bodies". The terms refer to aggregates of differentiated and undifferentiated cells that appear when pPS cells overgrow in plated or suspension cultures.

"Restricted developmental lineage cells" are cells derived from embryonic tissue, typically by differentiation or partial differentiation of pPS cells. These cells are capable of proliferating and differentiating into several different cell types, but the range of their repertory is restricted. Examples are hematopoietic cells, which are pluripotent for blood cell types, and hepatocyte progenitors, which are pluripotent for sinusoidal endothelial cells, hepatocytes, and potentially other liver cells. Another example is neural restricted cells, which can generate glial cell precursors that progress to oligodendrocytes and astrocytes, and neuronal precursors that progress to neurons.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. Also included are genetic alterations by any means that result in functionally altering or abolishing the action of an endogenous gene. The genetic alteration is said to be "inheritable" if progeny of the altered cell has the same alteration.

A "cell line" is a population of cells that can be propagated in culture through at least 10 passages. The population can be phenotypically homogeneous, or the population can be a mixture of measurably different phenotypes. Characteristics of the cell line are those characteristics of the population as a whole that are essentially unaltered after 10 passages.

A cell is described as "telomerized" if it has been genetically altered with a nucleic acid encoding a telomerase reverse transcriptase (TERT) of any species in such a manner that the TERT is transcribed and translated in the cell. The term also applies to progeny of the originally altered cell that have inherited the ability to express the TERT encoding region at an elevated level. The TERT encoding sequence is typically taken or adapted from a mammalian TERT gene, exemplified by human and mouse TERT, as indicated below.

A cell line is described as "permanent" or "immortalized" if it has at least one of the following properties: 1) it has been genetically altered for elevated expression of telomerase reverse transcriptase (TERT), detectable, for example, as increased telomerase activity in TRAP assay; 2) for cell lines otherwise capable of no more than 15 population doublings, it has been genetically altered to extend its replicative capacity under suitable culture conditions to at least 20 population doublings; or 3) for cell lines otherwise capable of more than 15 population doublings, it has been genetically altered to significantly extend the replicative capacity of the cell line under typical culture conditions. It is understood that cells meeting this definition include not only the original genetically altered cells, but also all progeny of such cells that meet the listed criteria.

The term "antibody" as used in this disclosure refers to both polyclonal and monoclonal antibody. The ambit of the term deliberately encompasses not only intact immunoglobulin molecules, but also fragments and derivatives of immunoglobulin molecules (such as single chain Fv constructs), and fragments and derivatives of immunoglobulin equivalents such as T-cell receptors, as may be prepared by techniques known in the art, and retaining the desired antigen binding specificity.

General Techniques

For further elaboration of general techniques useful in the practice of this invention, the practitioner can refer to standard textbooks and reviews in cell biology, tissue culture, and embryology. Included are *Teratocarcinomas and embryonic stem cells: A practical approach* (E. J. Robertson, ed., IRL Press Ltd. 1987); *Guide to Techniques in Mouse Development* (P. M. Wasserman et al., eds., Academic Press 1993); *Embryonic Stem Cell Differentiation in Vitro* (M. V. Wiles, Meth. Enzymol. 225:900, 1993); *Properties and uses of Embryonic Stem Cells: Prospects for Application to Human Biology and Gene Therapy* (P. D. Rathjen et al., al., 1993). Differentiation of stem cells is reviewed in Robertson, Meth. Cell Biol. 75:173, 1997; and Pedersen, Reprod. Fertil. Dev. 10:31, 1998.

Methods in molecular genetics and genetic engineering are described generally in the current editions of *Molecular Cloning: A Laboratory Manual*, (Sambrook et al.); *Oligonucleotide Synthesis* (M. J. Gait, ed.,); *Animal Cell Culture* (R. I. Freshney, ed.); *Gene Transfer Vectors for Mammalian Cells* (Miller & Calos, eds.); *Current Protocols in Molecular Biology* and *Short Protocols in Molecular Biology, 3rd Edition* (F. M. Ausubel et al., eds.); and *Recombinant DNA Methodology* (R. Wu ed., Academic Press). Reagents, cloning vectors, and kits for genetic manipulation referred to in this disclosure are available from commercial vendors such as BioRad, Stratagene, Invitrogen, and ClonTech.

For general techniques involved in preparation of mRNA and cDNA libraries and their analysis, those skilled in the art have access to *RNA Methodologies: A Laboratory Guide for Isolation and Characterization* (R. E. Farrell, Academic Press, 1998); *cDNA Library Protocols* (Cowell & Austin, eds., Humana Press); *Functional Genomics* (Hunt & Livesey, eds., 2000); and the *Annual Review of Genomics and Human Genetics* (E Lander, ed., published yearly by Annual Reviews). General techniques used in raising, purifying and modifying antibodies, and the design and execution of immunoassays including immunocytochemistry, the reader is referred to *Handbook of Experimental Immunology* (Weir & Blackwell, eds.); *Current Protocols in Immunology* (Coligan et al., eds.); and *Methods of Immunological Analysis* (Masseyeff et al., eds., Weinheim: VCH Verlags GmbH).

General techniques in cell culture and media collection are outlined in *Large Scale Mammalian Cell Culture* (Hu et al., Curr. Opin. Biotechnol. 8:148, 1997); *Serum-free Media* (K. Kitano, Biotechnology 17:73, 1991); *Large Scale Mammalian Cell Culture* (Curr. Opin. Biotechnol. 2:375, 1991); and *Suspension Culture of Mammalian Cells* (Birch et al., Bioprocess Technol. 19:251, 1990).

Sources of Pluripotent Stem Cells

Suitable source cells for culturing and differentiation according to this invention include established lines of pluripotent cells derived from tissue formed after gestation. Exemplary primary tissue sources are embryonic tissue (such as a blastocyst), or fetal tissue taken any time during gestation, typically but not necessarily before 10 weeks gestation. Non-limiting exemplars are established lines of primate embryonic stem (ES) and embryonic germ (EG) cells. Also contemplated is use of the techniques of this disclosure during the initial establishment or stabilization of such cells, in which case the source cells would be primary pluripotent cells taken directly from the tissues listed.

Media and Feeder Cells

Media for isolating and propagating pPS cells can have any of several different formulas, as long as the cells obtained have the desired characteristics, and can be propagated further. Suitable sources are as follows: Dulbecco's modified Eagles medium (DMEM), Gibco #11965-092; Knockout Dulbecco's modified Eagles medium (KO DMEM), Gibco #10829-018; 200 mM L-glutamine, Gibco #15039-027; non-essential amino acid solution, Gibco 11140-050; β-mercaptoethanol, Sigma # M7522; human recombinant basic fibroblast growth factor (bFGF), Gibco #13256-029. Exemplary serum-containing ES medium is made with 80% DMEM (typically KO DMEM), 20% defined fetal bovine serum (FBS) not heat inactivated, 0.1 mM non-essential amino acids, 1 mM L-glutamine, and 0.1 mM β-mercaptoethanol. The medium is filtered and stored at 4° C. Serum-free ES medium is made with 80% KO DMEM, 20% serum replacement, 0.1 mM non-essential amino acids, 1 mM L-glutamine, and 0.1 mM β-mercaptoethanol. Not all serum replacements work; an effective serum replacement is Gibco #10828-028 (proprietary formula; product obtainable from the manufacturer). The medium is filtered and stored at 4° C. Just before use, human bFGF is added to a final concentration of 4 ng/mL.

pPS cells are typically cultured on a layer of feeder cells that support the pPS cells in various ways, such as the production of soluble factors that promote pPS cell survival or proliferation, or inhibit differentiation. Feeder cells are typically fibroblast type cells, often derived from embryonic or fetal tissue. A frequently used source is mouse embryo. Useful feeder cell lines have been obtained by obtaining embryonic fibroblasts, transfecting them to express telomerase, and then passaging them or freezing them for future use. The cell lines are plated to near confluence, irradiated to prevent proliferation, and used to support pPS cell cultures.

In one illustration, pPS cells are first derived and supported on primary embryonic fibroblasts. Mouse embryonic fibroblasts (mEF) can be obtained from outbred CF1 mice (SASCO) or other suitable strains. The abdomen of a mouse at 13 days of pregnancy is swabbed with 70% ethanol, and the decidua is removed into phosphate buffered saline (PBS). Embryos are harvested; placenta, membranes, and soft tissues are removed; and the carcasses are washed twice in PBS. They are then transferred to fresh 10 cm bacterial dishes containing 2 mL trypsin/EDTA, and finely minced. After incubating 5 min at 37° C., the trypsin is inactivated with 5 mL DMEM containing 10% FBS, and the mixture is transferred to a 15 mL conical tube. Debris is allowed to settle for 2 min, the supernatant is made up to a final volume of 10 mL, and plated onto a 10 cm tissue culture plate or T75 flask. The flask is incubated undisturbed for 24 h, after which the medium is replaced. When flasks are confluent (~2-3 d), they are split 1:2 into new flasks.

Feeder cells are propagated in mEF medium, containing 90% DMEM (Gibco #11965-092), 10% FBS (Hyclone #30071-03), and 2 mM glutamine. mEFs are propagated in T150 flasks (Corning #430825), splitting the cells 1:2 every other day with trypsin, keeping the cells subconfluent. To prepare the feeder cell layer, cells are irradiated at a dose to inhibit proliferation but permit synthesis of important factors that support hES cells (4000 rads gamma irradiation). Six-well culture plates (such as Falcon #304) are coated by incubation at 37° C. with 1 mL 0.5% gelatin per well overnight, and plated with ~375,000 irradiated mEFs per well. Feeder cell layers are used 5 h to 4 days after plating. The medium is replaced with fresh hES medium just before seeding pPS cells.

Preparation of Human Embryonic Stem (hES) Cells

Human embryonic stem (hES) cells can be prepared as described by Thomson et al. (U.S. Pat. No. 5,843,780; Science 282:1145, 1998; Curr. Top. Dev. Biol. 38:133 ff., 1998; Proc. Natl. Acad. Sci. USA 92:7844, 1995).

Briefly, human blastocysts are obtained from human in vivo preimplantation embryos. Alternatively, in vitro fertilized (IVF) embryos can be used, or one cell human embryos can be expanded to the blastocyst stage (Bongso et al., Hum Reprod 4: 706, 1989). Human embryos are cultured to the blastocyst stage in G1.2 and G2.2 medium (Gardner et al., Fertil. Steril. 69:84, 1998). Blastocysts that develop are selected for ES cell isolation. The zona pellucida is removed from blastocysts by brief exposure to pronase (Sigma). The inner cell masses are isolated by immunosurgery, in which blastocysts are exposed to a 1:50 dilution of rabbit anti-human spleen cell antiserum for 30 minutes, then washed for 5 minutes three times in DMEM, and exposed to a 1:5 dilution of Guinea pig complement (Gibco) for 3 min (see Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps either by exposure to calcium and magnesium-free phosphate-buffered saline (PBS) with 1 mM EDTA, by exposure to dispase or trypsin, or by mechanical dissociation with a micropipette; and then replated on mEF in fresh medium. Dissociated cells are replated on mEF feeder layers in fresh ES medium, and observed for colony formation. Colonies demonstrating undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1-2 weeks by brief trypsinization, exposure to Dulbecco's PBS (without calcium or magnesium and with 2 mM EDTA), exposure to type IV collagenase (~200 U/mL; Gibco) or by selection of individual colonies by micropipette. Clump sizes of about 50 to 100 cells are optimal.

Preparation of Human Embryonic Germ (hEG) Cells

Human Embryonic Germ (hEG) cells can be prepared from primordial germ cells present in human fetal material taken about 8-11 weeks after the last menstrual period. Suitable preparation methods are described in Shamblott et al., Proc. Natl. Acad. Sci. USA 95:13726, 1998 and U.S. Pat. No. 6,090,622.

Briefly, genital ridges are rinsed with isotonic buffer, then placed into 0.1 mL 0.05% trypsin/0.53 mM sodium EDTA solution (BRL) and cut into <1 mm³ chunks. The tissue is then pipetted through a 100 μL tip to further disaggregate the cells. It is incubated at 37° C. for ~5 min, then ~3.5 mL EG growth medium is added. EG growth medium is DMEM, 4500 mg/L D-glucose, 2200 mg/L mM sodium bicarbonate; 15% ES qualified fetal calf serum (BRL); 2 mM glutamine (BRL); 1 mM sodium pyruvate (BRL); 1000-2000 U/mL human recombinant leukemia inhibitory factor (LIF, Genzyme); 1-2 ng/ml human recombinant basic fibroblast growth factor (bFGF, Genzyme); and 10 μM forskolin (in 10% DMSO). In an alternative approach, EG cells are isolated using hyaluronidase/collagenase/DNAse. Gonadal anlagen or genital ridges with mesenteries are dissected from fetal material, the genital ridges are rinsed in PBS, then placed in 0.1 ml HCD digestion solution (0.01% hyaluronidase type V, 0.002% DNAse I, 0.1% collagenase type IV, all from Sigma prepared in EG growth medium). Tissue is minced and incubated 1 h or overnight at 37° C., resuspended in 1-3 mL of EG growth medium, and plated onto a feeder layer.

Ninety-six well tissue culture plates are prepared with a sub-confluent layer of feeder cells cultured for 3 days in modified EG growth medium free of LIF, bFGF or forskolin, inactivated with 5000 rad γ-irradiation. Suitable feeders are STO cells (ATCC Accession No. CRL 1503). ~0.2 mL of primary germ cell (PGC) suspension is added to each of the wells. The first passage is conducted after 7-10 days in EG growth medium, transferring each well to one well of a 24-well culture dish previously prepared with irradiated STO mouse fibroblasts. The cells are cultured with daily replacement of medium until cell morphology consistent with EG cells are observed, typically after 7-30 days or 1-4 passages.

Propagation of pPS Cells pPS cells can be propagated continuously in culture, using a combination of culture conditions that support proliferation without promoting differentiation. It has been determined that hES cells can be grown without differentiation, even in the absence of feeder cells. For feeder-free culture, it is beneficial to provide a compatible culture surface (the substrate), and a nutrient medium that supplies some of the influences provided by the feeder cells.

Particularly suitable as a substrate for feeder-free pPS culture are extracellular matrix components (derived from basement membrane, or forming part of adhesion molecule receptor-ligand couplings). A commercial preparation is available from Becton Dickenson under the name Matrigel®, and can be obtained in regular or Growth Factor Reduced formulation. Both formulations are effective. Matrigel® is a soluble preparation from Engelbreth-Holm-Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations. Laminins are major components of all basal laminae in vertebrates, which interact with integrin heterodimers such as α6β1 and α6β4 (specific for laminins) and other heterodimers (that cross-react with other matrices). Using culture conditions illustrated in the examples, collagen IV supports hES cell growth, while collagen I does not. Substrates that can be tested using the experimental procedures described herein include not only other extracellular matrix components, but also polyamines (such as poly-ornithine, poly-lysine), and other commercially available coatings.

The pluripotent cells are plated onto the substrate in a suitable distribution and in the presence of a medium that promotes cell survival, propagation, and retention of the desirable characteristics. These characteristics benefit from careful attention to the seeding distribution. One feature of the distribution is the plating density. It has been found that plating densities of at least ~15,000 cells cm$^{-2}$ promote survival and limit differentiation. Typically, a plating density of between about 90,000 cm$^{-2}$ and about 170,000 cm$^{-2}$ is used.

Another feature is the dispersion of cells. The propagation of mouse stem cells involves dispersing the cells into a single-cell suspension (Robinson, Meth. Mol. Biol. 75:173, 1997 at page 177). In contrast, passaging primate PS cells has previously thought to require keeping the cells together in small clusters. Enzymatic digestion is halted before cells become completely dispersed (say, ~5 min with collagenase IV). The plate is then scraped gently with a pipette, and the cells are triturated with the pipette until they are suspended as clumps of adherent cells, about 10-2000 cells in size. The clumps are then plated directly onto the substrate without further dispersal.

It has been discovered that primate PS cells can be passaged between feeder-free cultures as a finer cell suspension, providing that an appropriate enzyme and medium are chosen, and the plating density is sufficiently high. By way of illustration, confluent human embryonic stem cells cultured in the absence of feeders are removed from the plates by incubating with a solution of 0.05% (wt/vol) trypsin (Gibco) and 0.053 mM EDTA for 5-15 min at 37° C. With the use of pipette, the remaining cells in the plate are removed and the cells are triturated with the pipette until the cells are dispersed into a suspension comprising single cells and some small clusters. The cells are then plated at densities of 50,000-200,000 cells/cm$^2$ to promote survival and limit differentiation. The phenotype of ES cells passaged by this technique is similar to what is observed when cells are harvested as clumps by collagen digestion. As another option, the cells can be harvested without enzymes before the plate reaches confluence. The cells are incubated ~5 min in a solution of 0.5 mM EDTA alone in PBS, washed from the culture vessel, and then plated into a new culture without further dispersal.

pPS cells plated in the absence of fresh feeder cells benefit from being cultured in a nutrient medium. The medium will generally contain the usual components to enhance cell survival, including isotonic buffer, essential minerals, and either serum or a serum replacement of some kind. Particularly beneficial is a medium that has been conditioned to supply some of the elements otherwise provided by feeder cells.

Feeder cells typically contain fibroblast type cells. Primary embryonic or fetal feeder cell cultures are a mixed population of cells, containing cells that have morphology of fibroblasts and of early muscle and neuronal cells. Different cells in the population may play different roles in supporting pPS culture, and the distribution and character of the culture may change.

As an alternative to primary mouse fibroblast cultures, conditioned medium can be prepared from other cell types, such as established cell lines. More permanent feeder cell lines can be developed for producing medium according to this invention using embryonic fibroblasts from a non-human species such as a mouse, genetically altered with an immortalizing gene, such as a gene that expresses telomerase.

It has also been discovered that cells with particular characteristics differentiated from human embryo derived cells can be used to support culture of undifferentiated pPS cells. Certain fibroblast-like cells or mesenchymal cells derived from human embryo cells have this property, and can be identified according to the assay described earlier. An exemplary method for obtaining suitable cells involves differentiating a culture of pPS cells (such as hES cells). Differentiated cells with a particular phenotype are selected from amongst the mixed differentiated cell population, and medium conditioned by culturing with the selected cells is tested for its ability to support growth of pPS cells in a culture environment essentially free of feeder cells. As illustrated in the examples below, medium that has been conditioned for 1-2 days is typically used to support pPS cell culture for 1-2 days, and then exchanged. Conditioned medium is used to support pPS cells undiluted, or titrated to an effective level of dilution. The conditioned medium can be supplemented before use with additional growth factors that benefit pPS cell culture. It is often beneficial to add growth factors such as bFGF or FGF-4 to the medium both before conditioning, and then again before using the medium to support the growth of pPS cells.

It should be recognized that each of the conditions described here can be optimized independently, and certain combinations of conditions will prove effective upon further testing. Such optimization is a matter of routine experimentation, and does not depart from the spirit of the invention provided in this disclosure.

Characteristics of pPS Cells

Human ES cells have the characteristic morphological features of undifferentiated stem cells. In the two dimensions of a standard microscopic image, hES cells have high nuclear/cytoplasmic ratios in the plane of the image, prominent nucleoli, and compact colony formation with poorly discernable cell junctions. Cell lines can be karyotyped using a standard G-banding technique (available at many clinical diagnostics labs that provides routine karyotyping services, such as the Cytogenetics Lab at Oakland Calif.) and compared to published human karyotypes. It is desirable to obtain cells that have a "normal karyotype", which means that the cells are euploid, wherein all human chromosomes are present and are not noticeably altered.

hES and hEG cells can also be characterized by expressed cell markers. In general, the tissue-specific markers discussed in this disclosure can be detected using a suitable immunological technique—such as flow cytometry for membrane-bound markers, immunocytochemistry for intracellular markers, and enzyme-linked immunoassay, for markers secreted into the medium. The expression of protein markers can also be detected at the mRNA level by reverse transcriptase-PCR using marker-specific primers. See U.S. Pat. No. 5,843,780 for further details.

Stage-specific embryonic antigens (SSEA) are characteristic of certain embryonic cell types. Antibodies for SSEA-1, SSEA-3 and SSEA-4 are available from the Developmental Studies Hybridoma Bank of the National Institute of Child Health and Human Development (Bethesda Md.). Other useful markers are detectable using antibodies designated Tra-1-60 and Tra-1-81 (Andrews et al., *Cell Lines from Human Genn Cell Tumors*, in E. J. Robertson, 1987, supra). Mouse ES cells can be used as a positive control for SSEA-1, and as a negative control for SSEA-4, Tra-1-60, and Tra-1-81. SSEA-4 is consistently present on human embryonal carcinoma (hEC) cells. Differentiation of pPS cells in vitro results in the loss of SSEA-4, Tra-1-60, and Tra-1-81 expression and increased expression of SSEA-1. SSEA-1 is also found on hEG cells. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.). Expression of hTERT and OCT-4 (detectable by RT-PCR) and telomerase activity (detectable by TRAP assay) are also characteristic of many types of undifferentiated pPS cells.

Where it is desirable to increase the replicative capacity of pPS cells, or cells differentiated from them, they can be immortalized or telomerized (either before or after differentiation) using the methods described below.

Differentiation of Propagated pPS Cells

This invention provides a new system for differentiating pPS cells into committed precursor cells or fully differentiated cells without forming embryoid bodies as an intermediate step.

Culturing embryoid bodies according to traditional methods are reported in O'Shea, Anat. Rec. (New Anat. 257:323, 1999). pPS cells are cultured in a manner that permits aggregates to form, for which many options are available: for example, by overgrowth of a donor pPS cell culture, or by culturing pPS cells in suspension in culture vessels having a substrate with low adhesion properties which allows EB formation. pPS cells are harvested by brief collagenase digestion, dissociated into clusters, and plated in non-adherent cell culture plates. The aggregates are fed every few days, and then harvested after a suitable period, typically 4-8 days.

The cells can then be cultured in a medium and/or on a substrate that promotes enrichment of cells of a particular lineage. The substrate can comprise matrix components such as Matrigel® (Becton Dickenson), laminin, collagen, gelatin, or matrix produced by first culturing a matrix-producing cell line (such as a fibroblast or endothelial cell line), and then lysing and washing in such a way that the matrix remains attached to the surface of the vessel. Embryoid bodies comprise a heterogeneous cell population, potentially having an endoderm exterior, and a mesoderm and ectoderm interior.

The Direct Differentiation Method

It has now been discovered that pPS cells can be differentiated into committed precursor cells or terminally differentiated cells without forming embryoid bodies or aggregates as an intermediate step.

Briefly, a suspension of undifferentiated pPS cells is prepared, and then plated onto a solid surface that promotes differentiation. In general, cultures of pPS cells are typically harvested when they have proliferated to an adequate density, but not to the point of over-confluence, because the cells will differentiate in an uncontrolled fashion if allowed to overgrow. A suitable suspension can be prepared by incubating the culture dish with Collagenase IV for about 5-20 min, and then scraping the cells from the dish. The cells can be dissociated, for example, by triturating in a pipette. For many types of differentiation, it is recommended that the cells not be completely dissociated, so that the majority of pPS is in clumps of about 10 to 200 cells.

The suspension is then plated onto a substrate that promotes regulated differentiation into committed precursor cells. Suitable substrates include glass or plastic surfaces that are adherent. For example, glass coverslips can be coated with a poly-cationic substance, such as a polyamine like poly-lysine, poly-ornithine, or other homogeneous or mixed polypeptides or other polymers with a predominant positive charge. The cells are then cultured in a suitable nutrient medium that is adapted to promote differentiation towards the desired cell lineage.

In some instances, differentiation is promoted by withdrawing serum or serum replacement from the culture medium. This can be achieved by substituting a medium devoid of serum and serum replacement, for example, at the time of replating, by withdrawing one or more components of the medium that promotes growth of undifferentiated cells or inhibits differentiation. Examples include certain growth factors, mitogens, leukemia inhibitory factor (LIF), fibroblast growth factors such as bFGF, and other components in conditioned medium. The new medium is said to be "essentially free" of these components when it contains <5% and preferably <1% of the usual concentration of the component used in culturing the cells in an undifferentiated form.

In some instances, differentiation is promoted by adding a medium component that promotes differentiation towards the desired cell lineage, or inhibits the growth of cells with undesired characteristics. For example, to generate cells committed to neural or glial lineages, the medium can include any of the following factors or medium constituents in an effective combination: Brain derived neurotrophic factor (BDNF), neutrotrophin-3 (NT-3), NT-4, epidermal growth factor (EGF), ciliary neurotrophic factor (CNTF), nerve growth factor (NGF), retinoic acid (RA), sonic hedgehog, FGF-8, ascorbic acid, forskolin, fetal bovine serum (FBS), and bone morphogenic proteins (BMPs). Other exemplary factors are listed in Example 5.

Under appropriate conditions, the direct differentiation method provides a cell population that is less heterogeneous than what is typically found in embryoid body derived cells. Unless explicitly indicated otherwise, the method can include a small degree of overgrowth, aggregate formation, or formation of occasional embryoid body-like structure—however, this is a collateral occurrence, and not required for differentiation of the cells into the committed precursor or terminally differentiated cell population desired. Typically, less than ~10% of the differentiated cell population will be progeny of cells that grew out of embryoid bodies, with levels of less than ~3% or ~1% being achievable in certain circumstances.

General principals for obtaining tissue cells from pluripotent stem cells are reviewed in Pedersen (Reprod. Fertil. Dev. 6:543, 1994), and U.S. Pat. No. 6,090,622. For neural progenitors, neural restrictive cells and glial cell precursors, see Bain et al., Biochem. Biophys. Res. Commun. 200:1252, 1994; Trojanowski et al., Exp. Neurol. 144:92, 1997; Wojcik et al., Proc. Natl. Acad. Sci. USA 90:1305-130; Mujtaba et al., Dev. Biol. 214:113, 1999; and U.S. Pat. Nos. 5,851,832, 5,928,947, 5,766,948, and 5,849,553. For cardiac muscle and cardiomyocytes see Chen et al., Dev. Dynamics 197: 217, 1993 and Wobus et al., Differentiation 48:173, 1991. For hematopoietic progenitors, see Burkert et al., New Biol. 3:698, 1991 and Biesecker et al., Exp. Hematol. 21:774, 1993. U.S. Pat. No. 5,773,255 relates to glucose-responsive insulin secreting pancreatic beta cell lines. U.S. Pat. No. 5,789,246 relates to hepatocyte precursor cells. Other progenitors of interest include but are not limited to chondrocytes, osteoblasts, retinal pigment epithelial cells, fibroblasts, skin cells such as keratinocytes, dendritic cells, hair follicle cells, renal duct epithelial cells, smooth and skeletal muscle cells, testicular progenitors, and vascular endothelial cells.

Scientists at Geron Corporation have discovered that culturing pPS cells or embryoid body cells in the presence of ligands that bind growth factor receptors promotes enrichment for neural precursor cells. The growth environment may contain a neural cell supportive extracellular matrix, such as fibronectin. Suitable growth factors include but are not limited to EGF, bFGF, PDGF, IGF-1, and antibodies to receptors for these ligands. Cofactors such as retinoic acid may also be included. The cultured cells may then be optionally separated based on whether they express a marker such as A2B5. Under the appropriate circumstances, populations of cells enriched for expression of the A2B5 marker may have the capacity to generate both neuronal cells (including mature neurons), and glial cells (including astrocytes and oligodendrocytes.

Optionally, the cell populations are further differentiated, for example, by culturing in a medium containing an activator of cAMP. Factors useful in the direct differentiation method for producing neurons are explored in Example 5, below. Markers for identifying cell types include β-tubulin III or microtubule-associated protein 2 (MAP-2), characteristic of neurons; glial fibrillary acidic protein (GFAP), present in astrocytes; galactocerebroside (GalC) or myelin basic protein (MBP); characteristic of oligodendrocytes; OCT-4, characteristic of undifferentiated hES cells; Nestin or Musashi, characteristic of neural precursors and other cells; and both A2B5 and NCAM, which appear on populations of neural precursors differentiated from pPS cells.

Scientists at Geron Corporation have also discovered that culturing pPS cells or embryoid body cells in the presence of a hepatocyte differentiation agent promotes enrichment for hepatocyte-like cells. The growth environment may contain a hepatocyte supportive extracellular matrix, such as collagen or Matrigel®. Suitable differentiation agents include various isomers of butyrate and their analogs, exemplified by n-butyrate. The cultured cells are optionally cultured simultaneously or sequentially with a hepatocyte maturation factor, such as an organic solvent like dimethyl sulfoxide (DMSO); a maturation cofactor such as retinoic acid; or a cytokine or hormone such as a glucocorticoid, epidermal growth factor (EGF), insulin, transforming growth factors (TGF-α and TGF-β), fibroblast growth factors (FGF), heparin, hepatocyte growth factors (HGF), interleukins (IL-1 and IL-6), insulin-like growth factors (IGF-I and IGF-II), and heparin-binding growth factors (HBGF-1).

Characteristics of Differentiated Cells

Cells can be characterized according to a number of phenotypic criteria. The criteria include but are not limited to characterization of morphological features, detection or quantitation of expressed cell markers and enzymatic activity, and determination of the functional properties of the cells in vivo.

Markers of interest for neural cells include β-tubulin III or neurofilament, characteristic of neurons; glial fibrillary acidic protein (GFAP), present in astrocytes; galactocerebroside (GalC) or myelin basic protein (MBP); characteristic of oligodendrocytes; Oct-4, characteristic of undifferentiated hES cells; nestin, characteristic of neural precursors and other cells. A2B5 and NCAM are characteristic of glial progenitors and neural progenitors, respectively. Cells can also be tested for secretion of characteristic biologically active substances. For example, GABA-secreting neurons can be identified by production of glutamic acid decarboxylase or GABA. Dopaminergic neurons can be identified by production of dopa decarboxylase, dopamine, or tyrosine hydroxylase.

Markers of interest for liver cells include α-fetoprotein (liver progenitors); albumin, $\alpha_1$-antitrypsin, glucose-6-phosphatase, cytochrome p450 activity, transferrin, asialoglycoprotein receptor, and glycogen storage (hepatocytes); CK7, CK19, and γ-glutamyl transferase (bile epithelium). It has been reported that hepatocyte differentiation requires the transcription factor HNF-4α (Li et al., Genes Dev. 14:464, 2000). Markers independent of HNF-4α expression include $\alpha_1$-antitrypsin, α-fetoprotein, apoE, glucokinase, insulin growth factors 1 and 2, IGF-1 receptor, insulin receptor, and leptin. Markers dependent on HNF-4α expression include albumin, apoAI, apoAII, apoB, apoCIII, apoCII, aldolase B, phenylalanine hydroxylase, L-type fatty acid binding protein, transferrin, retinol binding protein, and erythropoietin (EPO). Hepatocyte lineage cells differentiated from pPS cells will typically display at least three of the following markers: $\alpha_1$-antitrypsin (AAT) synthesis, albumin synthesis, asialoglycoprotein receptor (ASGR) expression, absence of α-fetoprotein, evidence of glycogen storage, evidence of cytochrome p450 activity, and evidence of glucose-6-phosphatase activity.

Markers of interest for other cell types include the following. For cardiomyocytes: GATA-4, Nkx2.5, cardiac troponin I, ANF, α-cardiac myosin heavy chain (α-MHC), actin, or ventricular myosin light chain 2 (MLC-2v). See Wobus et al., J. Mol. Cell Cardiol. 29:1525, 1997. For skeletal muscle: myoD, myogenin, and myf-5. For endothelial cells: PECAM (platelet endothelial cell adhesion molecule), Flk-1, tie-1, tie-2, vascular endothelial (VE) cadherin, MECA-32, and MEC-14.7. For smooth muscle cells: specific myosin heavy chain. For pancreatic cells, pdx and insulin secretion. For hematopoietic cells and their progenitors: GATA-1, CD34, β-major globulin, and β-major globulin like gene βH1.

Certain tissue-specific markers listed in this disclosure or known in the art can be detected by immunological techniques—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. Sequence data for the particular markers listed in this disclosure can be obtained from public databases such as GenBank (URL www.ncbi.nlm.nih.gov:80/entrez). Expression of tissue-specific markers as detected at the protein or mRNA level is considered positive if the level is at least 2-fold, and preferably more than 10- or 50-fold above that of a control cell, such as an undifferentiated pPS cell, a fibroblast, or other unrelated cell type.

The system provided by this invention allows production of a relatively uniform cell population, without the complexity of cells often obtained by forming embryoid bodies. Cell populations derived by direct differentiation may be 50%, 75%, 90%, or 98% homogeneous in terms of morphological characteristics of the desired cell type, or expression of any of the markers indicated above. They may also be relatively devoid of undesired cell types, such as endothelial cells, mesenchymal cells, fibroblasts, smooth muscle cells, cells expressing α-myosin heavy chain, or other particular cell types of the endoderm, mesoderm, or ectoderm.

Modifying Differentiated Cells

Differentiated cells of this invention can be genetically altered in a manner that permits the genetic alteration to be either transient, or stable and inheritable as the cells divide. Undifferentiated cells can be genetically altered and then differentiated into the desired phenotype, or the cells can be differentiated first before genetic alteration.

Where the pPS cells are genetically altered before differentiation, the genetic alteration can be performed on a permanent feeder cell line that has resistance genes for drugs used to select for transformed cells, or on pPS cells grown in feeder-free culture.

Suitable methods for transferring vector plasmids into hES cells include lipid/DNA complexes, such as those described in U.S. Pat. Nos. 5,578,475; 5,627,175; 5,705,308; 5,744,335; 5,976,567; 6,020,202; and 6,051,429. Suitable reagents include lipofectamine, a 3:1 (w/w) liposome formulation of the poly-cationic lipid 2,3-dioleyloxy-N-[2 (sperminecarboxamido)ethyl]-N,N-dimethyl-1-propanaminium trifluoroacetate (DOSPA) (Chemical Abstracts Registry name: N-[2-(2,5-bis[β-aminopropyl)amino]-1-oxpentyl}amino) ethyl]-N,N-dimethyl-2,3-bis(9-octadecenyloxy)-1-propanaminium trifluoroacetate), and the neutral lipid dioleoyl phosphatidylethanolamine (DOPE) in membrane filtered water. Exemplary is the formulation Lipofectamine2000™ (available from Gibco/Life Technologies #11668019). Other reagents include: FuGENE™ 6 Transfection Reagent (a blend of lipids in non-liposomal form and other compounds in 80% ethanol, obtainable from Roche Diagnostics Corp. #1814443); and LipoTAXI™ transfection reagent (a lipid formulation from Invitrogen Corp., #204110). Suitable viral vector systems for producing hES cells with stable genetic alterations are based on adenovirus and retrovirus, and may be prepared using commercially available virus components.

For therapeutic use, it is usually desirable that differentiated cell populations be substantially free of undifferentiated pPS cells. One way of depleting undifferentiated stem cells from the population is to transfect them with a vector in which an effector gene under control of a promoter that causes preferential expression in undifferentiated cells. Suitable promoters include the TERT promoter and the OCT-4 promoter. The effector gene may be directly lytic to the cell (encoding, for example, a toxin or a mediator of apoptosis). Alternatively, the effector gene may render the cell susceptible to toxic effects of an external agent, such as an antibody or a prodrug. Exemplary is a herpes simplex thymidine kinase (tk) gene, which causes cells in which it is expressed to be susceptible to ganciclovir. Suitable TERT promoter tk constructs are provided in WO 98/14593 (Morin et al.).

Increasing Replicative Capacity of Differentiated Cells

It is desirable that certain differentiated cells have the ability to replicate in certain drug screening and therapeutic applications. Cells can optionally be telomerized to increase their replication potential, either before or after they progress to restricted developmental lineage cells or terminally differentiated cells. pPS cells that are telomerized may be taken down the differentiation pathway described earlier; or differentiated cells can be telomerized directly.

Before and after telomerization, telomerase activity and expression of hTERT gene product can be determined using commercially available reagents and established methods. For example, pPS cells are evaluated for telomerase using TRAP activity assay (Kim et al., Science 266:2011, 1997; Weinrich et al., Nature Genetics 17:498, 1997). Expression of hTERT at the mRNA level is evaluated by RT-PCR.

Cells are telomerized by genetically altering them by transfection or transduction with a suitable vector, homologous recombination, or other appropriate technique, so that they express the telomerase catalytic component (TERT). Particularly suitable is the catalytic component of human telomerase (hTERT), provided in International Patent Publication WO 98/14592. For certain applications, species homologs like mouse TERT (WO 99/27113) can also be used. Transfection and expression of telomerase in human cells is described in Bodnar et al., Science 279:349, 1998 and Jiang et al., Nat. Genet. 21:111, 1999. In another example, hTERT clones (WO 98/14592) are used as a source of hTERT encoding sequence, and spliced into an EcoRI site of a PBBS212 vector under control of the MPSV promoter, or into the EcoRI site of commercially available pBABE retrovirus vector, under control of the LTR promoter. Differentiated or undifferentiated pPS cells are genetically altered using vector containing supernatants over a 8-16 h period, and then exchanged into growth medium for 1-2 days. Genetically altered cells are selected using 0.5-2.5 µg/mL puromycin, and recultured. They can then be assessed for hTERT expression by RT-PCR, telomerase activity (TRAP assay), immunocytochemical staining for hTERT, or replicative capacity. Continuously replicating colonies will be enriched by further culturing under conditions that support proliferation, and cells with desirable phenotypes can optionally be cloned by limiting dilution.

In certain embodiments of this invention, pPS cells are differentiated, and then genetically altered to express TERT. In other embodiments of this invention, pPS cells are genetically altered to express TERT, and then differentiated. Successful modification to increase TERT expression can be determined by TRAP assay, or by determining whether the replicative capacity of the cells has improved.

Other methods of immortalizing cells are also contemplated, such as transforming the cells with DNA encoding the SV40 large T antigen (U.S. Pat. No. 5,869,243, International Patent Publication WO 97/32972). Transfection with oncogenes or oncovirus products is less suitable when the cells are to be used for therapeutic purposes. Telomerized cells are of particular interest in applications of this invention where it is advantageous to have cells that can proliferate and maintain their karyotype—for example, in pharmaceutical screening, and in therapeutic protocols where differentiated or partially differentiated cells are administered to an individual as part of a protocol to achieve tissue regeneration.

Use of Differentiated Cells

This description provides a method by which large numbers of pluripotent cells can be produced commercially, and then differentiated into committed precursor cells or terminally differentiated cells. These cell populations can be used for a number of important research, development, and commercial purposes.

Preparation of Expression Libraries and Specific Antibody

The differentiated cells of this invention can also be used to prepare specific antibody for phenotypic markers of differentiated cells. Polyclonal antibodies can be prepared by injecting a vertebrate animal with cells of this invention in an immunogenic form. Production of monoclonal antibodies is described in such standard references as Harrow & Lane (1988), U.S. Pat. Nos. 4,491,632, 4,472,500 and 4,444,887, and *Methods in Enzymology* 73B:3 (1981). Other methods of obtaining specific antibody molecules (optimally in the form of single-chain variable regions) involve contacting a library of immunocompetent cells or viral particles with the target antigen, and growing out positively selected clones. See Marks et al., *New Eng. J. Med.* 335:730, 1996, International Patent Publications WO 94/13804, WO 92/01047, WO 90/02809, and McGuiness et al., *Nature Biotechnol.* 14:1449, 1996.

By positively selecting using pPS of this invention, and negatively selecting using cells bearing more broadly distributed antigens (such as differentiated embryonic cells) or adult-derived stem cells, the desired specificity can be obtained. The antibodies in turn can be used to identify or rescue cells of a desired phenotype from a mixed cell population, for purposes such as costaining during immunodiagnosis using tissue samples, and isolating precursor cells from terminally differentiated cells, and cells of other lineages.

Differentiated pPS cells of this invention can also be used to prepare mRNA and cDNA libraries that reflect the gene expression patterns of these cells. mRNA and cDNA can also be made from undifferentiated cells, and used to produce subtraction libraries enriched for transcripts that are up- or down-regulated during differentiation. Further information can be found in U.S. patent application Ser. No. 09/688,031.

Screening Proliferation Factors, Differentiation Factors, and Pharmaceuticals pPS cells can be used to screen for factors (such as small molecule drugs, peptides, polynucleotides, and the like) or conditions (such as culture conditions or manipulation) that affect the characteristics of pPS cells in culture. This system has the advantage of not being complicated by a secondary effect caused by perturbation of the feeder cells by the test compound. In one application, growth affecting substances are tested. The conditioned medium is withdrawn from the culture and a simpler medium (such as KO DMEM) is substituted. Different wells are then treated with different cocktails of soluble factors that are candidates for replacing the components of the conditioned medium. Efficacy of each mixture is determined if the treated cells are maintained and proliferate in a satisfactory manner, optimally as well as in conditioned medium. Potential differentiation factors or conditions can be tested by treating the cells according to the test protocol, and then determining whether the treated cell develops functional or phenotypic characteristics of a differentiated cell of a particular lineage.

Feeder-free pPS cultures can also be used for the testing of pharmaceutical compounds in drug research. Assessment of the activity of candidate pharmaceutical compounds generally involves combining the differentiated cells of this invention with the candidate compound, determining any resulting change, and then correlating the effect of the compound with the observed change. The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity (Castell et al., pp 375-410 in "In vitro Methods in Pharmaceutical Research," Academic Press, 1997). Cytotoxicity can be determined by the effect on cell viability, survival, and morphology, on the expression or release of certain markers, receptors or enzymes, on DNA synthesis or repair. measured by [$^3$H]-thymidine or BrdU incorporation, or on sister chromatid exchange, determined by metaphase spread. The reader is referred generally to the standard textbook "In vitro Methods in Pharmaceutical Research", Academic Press, 1997, and U.S. Pat. No. 5,030,015.

Genomics

Suitable methods for comparing expression at the protein level include the immunoassay or immunocytochemistry techniques described above. Suitable methods for comparing expression at the level of transcription include methods of differential display of mRNA (Liang et al., Cancer Res. 52:6966, 1992), and matrix array expression systems (Schena et al., Science 270:467, 1995; Eisen et al., Methods Enzymol. 303:179, 1999; Brown et al., Nat. Genet. 21 Suppl 1:33, 1999).

The use of microarray in analyzing gene expression is reviewed generally by Fritz et al Science 288:316, 2000; "Microarray Biochip Technology", M. Schena ed., Eaton Publishing Company; "Microarray analysis", Gwynne & Page, Science (Aug. 6, 1999 supplement); Pollack et al., Nat Genet 23:41, 1999; Gerhold et al., Trends Biochem. Sci. 24:168, 1999; "Gene Chips (DNA Microarrays)", L. Shi at the Internet URL www.Gene-Chips.com. Systems and reagents for performing microarray analysis are available commercially from companies such as Affymetrix, Inc., Santa Clara Calif.; Gene Logic Inc., Columbia Md.; HySeq Inc., Sunnyvale Calif.; Molecular Dynamics Inc., Sunnyvale Calif.; Nanogen, San Diego Calif.; and Synteni Inc., Fremont Calif. (acquired by Incyte Genomics, Palo Alto Calif.).

Solid-phase arrays are manufactured by attaching the probe at specific sites either by synthesizing the probe at the desired position, or by presynthesizing the probe fragment and then attaching it to the solid support. A variety of solid supports can be used, including glasses, plastics, ceramics, metals, gels, membranes, paper, and beads of various composition. U.S. Pat. No. 5,445,934 discloses a method of on-chip synthesis, in which a glass slide is derivatized with a chemical species containing a photo-cleavable protecting group. Each site is sequentially deprotected by irradiation through a mask, and then reacted with a DNA monomer containing a photoprotective group. Methods for attaching a presynthesized probe onto a solid support include adsorption, ultra violet linking, and covalent attachment. In one example, the solid support is modified to carry an active group, such as hydroxyl, carboxyl, amine, aldehyde, hydrazine, epoxide, bromoacetyl, maleimide, or thiol groups through which the probe is attached (U.S. Pat. Nos. 5,474,895 and 5,514,785).

The probing assay is typically conducted by contacting the array by a fluid potentially containing the nucleotide sequences of interest under suitable conditions for hybridization conditions, and then determining any hybrid formed. For example, mRNA or DNA in the sample is amplified in the presence of nucleotides attached to a suitable label, such as the fluorescent labels Cy3 or Cy5. Conditions are adjusted so that hybridization occurs with precise complementary matches or with various degrees of homology, as appropriate. The array is then washed, and bound nucleic acid is determined by measuring the presence or amount of label associated with the solid phase. Different samples can be compared between arrays for relative levels of expression, optionally standardized using genes expressed in most cells of interest, such as a ribosomal or housekeeping gene, or as a proportion of total polynucleotide in the sample. Alternatively, samples from two or more different sources can be tested simultaneously on the same array, by preparing the amplified polynucleotide from each source with a different label.

An exemplary method is conducted using a Genetic Microsystems array generator, and an Axon GenePix™ Scanner. Microarrays are prepared by first amplifying cDNA fragments encoding marker sequences to be analyzed in a 96 or 384 well format. The cDNA is then spotted directly onto glass slides at a density as high as >5,000 per slide. To compare mRNA preparations from two cells of interest, one preparation is converted into Cy3-labeled cDNA, while the other is converted into Cy5-labeled cDNA. The two cDNA preparations are hybridized simultaneously to the microarray slide, and then washed to eliminate non-specific binding. Any given spot on the array will bind each of the cDNA products in proportion to abundance of the transcript in the two original mRNA preparations. The slide is then scanned at wavelengths appropriate for each of the labels, the resulting fluorescence is quantified, and the results are formatted to give an indication of the relative abundance of mRNA for each marker on the array.

Identifying expression products for use in characterizing and affecting differentiated cells of this invention involves analyzing the expression level of RNA, protein, or other gene product in a first cell type, such as a pluripotent precursor cell, or a cell capable of differentiating along a particular pathway; then analyzing the expression level of the same product in a control cell type; comparing the relative expression level between the two cell types, (typically normalized by total protein or RNA in, the sample, or in comparison with another gene product expected to be expressed at a similar level in both cell types, such as a house-keeping gene); and then identifying products of interest based on the comparative expression level.

Products will typically be of interest if their relative expression level is at least about 2-fold, 10-fold, or 100-fold elevated (or suppressed) in differentiated pPS cells of this invention, in comparison with the control. This analysis can optionally be computer-assisted, by marking the expression level in each cell type on an independent axis, wherein the position of the mark relative to each axis is in accordance with the expression level in the respective cell, and then selecting a product of interest based on the position of the mark. Alternatively, the difference in expression between the first cell and the control cell can be represented on a color spectrum (for example, where yellow represents equivalent expression levels, red indicates augmented expression and blue represents suppressed expression). The product of interest can then be selected based on the color representing expression of one marker of interest, or based on a pattern of colors representing a plurality of markers.

Genes and proteins that undergo a change in expression level during differentiation are of interest for a number of purposes. For example, where expression is high in pPS cells and decreases during differentiation can be used as molecular markers of the undifferentiated state. Reagents corresponding to these markers, such as antibodies, can be used, for example, to eliminate undifferentiated pPS cells from a population of differentiated cells by immunoaffinity isolation or complement-mediated lysis. Where expression is increased during differentiation, the markers can be used in a similar manner to purify, enrich, remove or eliminate specific cell types derived from pPS cells. These markers may serve as indicators of broad classes of cell differentiation, such as genes or proteins expressed in mesodermal, endodermal or ectodermal lineages, or may serve as markers of highly differentiated cell types.

Genes that are upregulated during expression may also be useful to influence the differentiation of pPS cells into specific lineages. For instance, the forced expression in undifferentiated pPS cells of transgenes encoding transcription factors, growth factors, receptors and signaling molecules can be tested for an ability to influence differentiation into specific cell lineages.

Once the sequence of mRNA preferentially expressed or repressed in differentiated cells is determined, it can be used in the manufacture of polynucleotides that contain such sequences, polypeptides they encode, and antibody specific for the polypeptides. Oligonucleotides of less than ~50 base pairs are conveniently prepared by chemical synthesis, either through a commercial service or by a known synthetic method, such as solid phase synthesis (Hirose et al., *Tetra. Lett.* 19:2449-2452, 1978; U.S. Pat. No. 4,415,732). Polynucleotides can also be manufactured by PCR amplification using a template with the desired sequence (U.S. Pat. Nos. 4,683,195 and 4,683,202). Production scale amounts of large polynucleotides are conveniently obtained by inserting the desired sequence into a suitable cloning vector, and either reproducing the clone, or transfecting the sequence into a suitable host cell. Short polypeptides can be prepared by solid-phase chemical synthesis: see Dugas & Penney, Bioorganic Chemistry, Springer-Verlag NY pp 54-92 (1981).

Longer polypeptides are conveniently manufactured by translation in an in vitro translation system, or by expression in a suitable host cell (U.S. Pat. No. 5,552,524). Polyclonal and monoclonal antibody specific for polypeptides encoded by mRNA and cDNA of this invention can be obtained by determining amino acid sequence from a protein encoding region in an expression library, and immunizing an animal or contacting an immunocompetent cell or particle with a protein containing the determined sequence, according to standard techniques.

Therapeutic Compositions

Differentiated cells of this invention can also be used for tissue reconstitution or regeneration in a human patient in need thereof. The cells are administered in a manner that permits them to graft to the intended tissue site and reconstitute or regenerate the functionally deficient area.

In one example, neural stem cells are transplanted directly into parenchymal or intrathecal sites of the central nervous system, according to the disease being treated. Grafts are done using single cell suspension or small aggregates at a density of 25,000-500,000 cells per µL (U.S. Pat. No. 5,968,829). The efficacy of neural cell transplants can be assessed in a rat model for acutely injured spinal cord as described by McDonald et al. (Nat. Med. 5:1410, 1999. A successful transplant will show transplant-derived cells present in the lesion 2-5 weeks later, differentiated into astrocytes, oligodendrocytes, and/or neurons, and migrating along the cord from the lesioned end, and an improvement in gate, coordination, and weight-bearing.

The efficacy of cardiomyocytes can be assessed in an animal model for cardiac cryoinjury, which causes 55% of the left ventricular wall tissue to become scar tissue without treatment (Li et al., Ann. Thorac. Surg. 62:654, 1996; Sakai et al., Ann. Thorac. Surg. 8:2074, 1999, Sakai et al., J. Thorac. Cardiovasc. Surg. 118:715, 1999). Successful treatment will reduce the area of the scar, limit scar expansion, and improve heart function as determined by systolic, diastolic, and developed pressure. Cardiac injury can also be modeled using an embolization coil in the distal portion of the left anterior descending artery (Watanabe et al., Cell Transplant. 7:239, 1998), and efficacy of treatment can be evaluated by histology and cardiac function. Cardiomyocyte preparations embodied in this invention can be used in therapy to regenerate cardiac muscle and treat insufficient cardiac function (U.S. Pat. No. 5,919,449 and WO 99/03973).

Hepatocytes and hepatocyte precursors can be assessed in animal models for ability to repair liver damage. One such example is damage caused by intraperitoneal injection of D-galactosamine (Dabeva et al., Am. J. Pathol. 143:1606, 1993). Efficacy of treatment can be determined by immunocytochemical staining for liver cell markers, microscopic determination of whether canalicular structures form in growing tissue, and the ability of the treatment to restore synthesis of liver-specific proteins. Liver cells can be used in therapy by direct administration, or as part of a bioassist device that provides temporary liver function while the subject's liver tissue regenerates itself following fulminant hepatic failure.

Cells prepared according to this invention that are useful for human or veterinary therapy are optimally supplied in a pharmaceutical composition, comprising an isotonic excipient prepared under sufficiently sterile conditions for human administration. For general principles in medicinal formulation, the reader is referred to *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000. The compositions may be packaged with written instructions for use of the cells in tissue regeneration, or restoring a therapeutically important metabolic function.

The examples that follow are provided by way of further illustration, and are not meant to imply any limitation in the practice of the claimed invention.

EXAMPLES

Example 1

Feeder-free Passage of hES cells

Undifferentiated hES cells isolated on primary mouse embryonic feeder cells were propagated in the absence of feeder cells. The culture wells were coated with Matrigel®, and the cells were cultured in the presence of conditioned nutrient medium obtained from a culture of irradiated primary fibroblasts.

Preparation of Conditioned Media (CM) from Primary Mouse Embryonic Fibroblasts (mEF):

Fibroblasts were harvested from T150 flasks by washing once with $Ca^{++}/Mg^{++}$ free PBS and incubating in 1.5-2 mL trypsin/EDTA (Gibco) for about 5 min. After the fibroblasts detached from the flask, they were collected in mEF media (DMEM+10% FBS). The cells were irradiated at 4000 rad (508 sec at 140 kV: shelf setting 6 in a Torrex generator), counted and seeded at about 55,000 cells $cm^{-2}$ in mEF media (525,000 cells/well of a 6 well plate). After at least 4 hours the media were exchanged with SR containing ES media, using 3-4 mL per 9.6 $cm$ well of a 6 well plate. Conditioned media was collected daily for feeding of hES cultures. Alternatively, medium was prepared using mEF plated in culture flasks, exchanging medium daily at 0.3-0.4 mL $cm^{-2}$. Before addition to the hES cultures, the conditioned medium was supplemented with 4 ng/mL of human bFGF (Gibco). Fibroblast cultures were used in this system for about 1 week, before replacing with newly prepared cells.

Matrigel® Coating:

Growth Factor Reduced Matrigel® or regular Matrigel® (Becton-Dickinson, Bedford Mass.) was thawed at 4° C. The Matrigel® was diluted 1:10 to 1:500 (typically 1:30) in cold KO DMEM. 0.75-1.0 mL of solution was added to each 9.6 $cm^2$ well, and incubated at room temperature for 1 h, or at 4° C. at least overnight. The coated wells were washed once with cold KO DMEM before adding cells. Plates were used within 2 h after coating, or stored in DMEM at 4° C. and used within ~1 week.

Human ES Culture:

Undifferentiated hES colonies were harvested from hES cultures on feeders as follows. Cultures were incubated in ~200 U/mL collagenase IV for about 5 minutes at 37° C. Colonies were harvested by picking individual colonies up with a 20 µL pipet tip under a microscope or by scraping and dissociating into small clusters in conditioned medium (CM). These cells were then seeded onto Matrigel® in conditioned media at 15 colonies to each 9.6 $cm^2$ well (if 1 colony is ~10,000 cells, then the plating density is ~15,000 cells $cm^{-2}$).

The day after seeding on Matrigel®, hES cells were visible as small colonies (~100-2,000 cells) and there were cells in between the colonies that appeared to be differentiating or dying. As the hES cells proliferated, the colonies became quite large and very compact, representing the majority of surface area of the culture dish. The hES cells in the colonies had a high nucleus to cytoplasm ratio and had prominent nucleoli, similar to hES cells maintained on feeder cells. At confluence, the differentiated cells in between the colonies represented less than 10% of the cells in the culture.

Six days after seeding, the cultures had become almost confluent. The cultures were split by incubating with 1 mL~200 U/mL Collagenase IV solution in KO DMEM for ~5 minutes at 37° C. The collagenase solution was aspirated, 2 mL hES medium was added per well, and the hES cells were scraped from the dish with a pipette. The cell suspension was transferred to a 15 mL conical tube, brought up to a volume of 6 mL, and gently triturated to dissociate the cells into small clusters of 10-2000 cells. The cells were then re-seeded on Matrigel® coated plates in CM, as above. Cells were seeded at a 1:3 or 1:6 ratio, approximately 90,000 to 170,000 cells $cm^{-2}$, making up the volume in each well to 3 mL. Medium was changed daily, and the cells were split and passaged again at 13 d and again at 19 d after initial seeding.

Undifferentiated hES cells express SSEA-4, Tra-1-60, Tra-1-81, OCT-4, and hTERT. In order to assess whether the cells maintained in feeder-free conditions retained these markers, cells were evaluated by immunostaining, reverse transcriptase PCR amplification, and assay for telomerase activity. As assayed by fluorescence-activated cell sorting, cells on Matrigel®, laminin, fibronectin or collagen IV expressed SSEA-4, Tra-1-60 and Tra-1-81. There was very little expression of SSEA-1, a glycolipid that is not expressed by undifferentiated hES cells. Immunocytochemistry analysis shows that SSEA-4, Tra-1-60, Tra-1-81, and alkaline phosphatase were expressed by the hES colonies on Matrigel® or laminin, as seen for the cells on feeders—but not by the differentiated cells in between the colonies.

FIG. 1 shows OCT-1 and hTERT expression of H1 cells on feeders and off feeders, as detected by reverse-transcriptase PCR amplification. For radioactive relative quantification of individual gene products, QuantumRNA™ Alternate18S Internal Standard primers (Ambion, Austin Tex., USA) were employed according to the manufacturer's instructions. Briefly, the linear range of amplification of a particular primer pair was determined, then coamplified with the appropriate mixture of alternate18S primers:competimers to yield PCR products with coinciding linear ranges. Before addition of AmpliTaq™ (Roche) to PCR reactions, the enzyme was pre-incubated with the TaqStarr™ antibody (ProMega) according to manufacturer's instructions. Radioactive PCR reactions were analyzed on 5% non-denaturing polyacrylamide gels, dried, and exposed to phosphoimage screens (Molecular Dynamics) for 1 hour. Screens were scanned with a Molecular Dynamics Storm 860 and band intensities were quantified using ImageQuant™ software. Results are expressed as the ratio of radioactivity incorporated into the hTERT or OCT-4 band, standardized to the radioactivity incorporated into the 18s band.

Primers and amplification conditions for particular markers are as follows. OCT-4: Sense (SEQ. ID NO:1) 5'-CTTGCTGCAG AAGTGGGTGG AGGAA-3'; Antisense (SEQ. ID NO:2) 5'-CTGCAGTGTG GGTTTCGGGC A-3'; alternate18:competimers 1:4; 19 cycles (94° 30 sec; 60° 30 sec; 72° 30 sec). hTERT: Sense (SEQ. ID NO:3) 5'-CGGAAGAGTG TCTGGAGCAA-3'; Antisense (SEQ. ID NO:4) 5'-GGATGAAGCG GAGTCTGGA-3'; alternate18: competimers 1:12; 34 cycles (94° 30 sec; 60° 30 sec; 72° 30 sec).

The transcription factor OCT-4 is normally expressed in the undifferentiated hES cells and is down-regulated upon differentiation. The cells maintained on Matrigel® or laminin in conditioned medium (CM) for 21 days express OCT-4, whereas cells maintained in Matrigel® in unconditioned regular medium (RM) did not. Cells maintained on fibronectin or collagen IV, which showed a large degree of differentiation, expressed lower levels of OCT-4 compared to cells on feeders, Matrigel® or laminin.

Telomerase activity was measured by TRAP assay (Kim et al., Science 266:2011, 1997; Weinrich et al., Nature Genetics 17:498, 1997). All the cultures conditions showed positive telomerase activity after 40 days on Matrigel®, laminin, fibronectin or collagen IV in mEF conditioned medium.

Example 2

Direct Differentiation of hES Cells

Differentiation using standard methods of aggregate formation was compared with a technique of this invention in which cells are differentiated by plating directly onto a solid surface under certain conditions.

For the aggregate differentiation technique, monolayer cultures of rhesus and human ES lines were harvested by incubating in Collagenase IV for 5-20 min, and the cells were scraped from the plate. The cells were then dissociated and plated in non-adherent cell culture plates in FBS-containing medium (20% non-heat-inactivated FBS (Hyclone), supplemented with 0.1 mM non-essential amino acids, 1 mM glutamine, 0.1 mM β-mercaptoethanol. The EBs were fed every other day by the addition of 2 mL of medium per well (6 well plate). When the volume of medium exceeded 4 mL/well, the EBs were collected and resuspended in fresh medium. The plates were placed into a 37° C. incubator, and in some instances, a rocker was used to facilitate maintaining aggregates in suspension. After 4-8 days in suspension, aggregate bodies formed and were plated onto a substrate to allow for further differentiation.

For the direct differentiation technique, suspensions of rhesus and human ES cells were prepared in a similar fashion. The cells were then dissociated by trituration to clusters of ~50-100 cells, and plated onto glass coverslips treated with poly-ornithine. The cells were maintained in serum containing medium, or defined medium for 7-10 days before analysis. Cells were tested by immunoreactivity for β-tubulin III and MAP-2, which are characteristic of neurons, and glial fibrillary acidic protein (GFAP), which is characteristic of astrocytes.

Six different ES lines differentiated into cells bearing markers for neurons and astrocytes, using either the aggregate or direct differentiation technique. In cultures derived from rhesus ES cells, percentage of aggregates that contained neurons ranged from 49% to 93%. In cultures derived from human ES cells, the percentage of aggregates containing neurons ranged from 60% to 80%. Double labeling for GABA and Gβ-tubulin indicated that a sub-population of the neurons express the inhibitory neurotransmitter GABA. Astrocytes and oligodendrocytes were identified with GFAP immune reactivity and GalC immune reactivity, respectively. Therefore, the human and rhesus ES cells have the capacity to form all three major cell phenotypes in the central nervous system.

The effect of several members of the neurotrophin growth factor family was examined. hES cells were differentiated by harvesting with collagenase, dissociating, and reseeding onto poly-ornithine coated cover slips. The cells were plated into DMEM/F12+N2+10% FBS overnight. The following day, the serum was removed from the medium and replaced with 10 ng/mL human bFGF and the growth factor being tested. After 24 hours, bFGF was removed from the medium. These cultures were fed every other day. They were fixed after 7 days of differentiation and immunostained for analysis. The number of neurons was evaluated by counting cells positive for β-tubulin. Cultures maintained in the presence of 10 ng/mL brain derived neurotrophic factor (BDNF) formed approximately 3-fold more neurons than the control cultures. Cultures maintained in neurotrophin-3 (1 ng/mL) formed approximately 2-fold more neurons than control cultures.

To assess cardiomyocyte formation, EBs were transferred to gelatin-coated plates or chamber slides after 4 days in the suspension cultures. The EBs attached to the surface after seeding, proliferated and differentiated into different types of cells. Spontaneously contracting cells were observed in various regions of the culture at differentiation day 8 and the number of beating regions increased until about day 10. In some cases, more than 75% of the EBs had contracting regions. Beating cells were morphologically similar to mouse ES cell-derived beating cardiomyocytes. In these cultures 100% of the contracting areas were immunoreactive with cardiac troponin I (cTnI), while minimal immunoreactivity was observed in the non-beating cells.

Cultures of differentiated EBs were subjected to Western blot analysis using monoclonal antibody against cTnI. This assay gave a strong 31 kDa protein signal, corresponding to the size of the purified native human cTnI. It was detected in differentiated human ES cells containing contracting cells, but not in undifferentiated ES cells or differentiated cultures with no evidence of contracting cells. As a control, the blot was reprobed with β-actin specific antibody, confirming the presence of similar amounts of proteins in all samples.

In other experiments, EBs were cultured for 8 or 16 days and maintained as adherent cultures for an additional 10 days. RNA was prepared from the differentiated human ES cells and semiquantitative RT-PCR was performed to detect the relative expression of the endoderm-specific products $\alpha_1$-anti-trypsin, AFP, and albumin. Low levels of $\alpha_1$-anti-trypsin and AFP were detected in the undifferentiated cultures; little or no albumin was detected in the same cultures. All 3 markers were detected at significantly higher levels after differentiation. Expression of all 3 endoderm markers was higher in cultures derived from 8 day embryoid bodies than 16 day embryoid bodies.

Example 3

Direct Differentiation of hES to Hepatocyte-like Cells without Forming Embryoid Bodies This experiment demonstrated the use of the direct differentiation technique for deriving human ES cells into a relatively uniform population of cells with phenotypic markers of hepatocytes.

The hES cells were maintained in undifferentiated culture conditions (Matrigel® plus mEF conditioned medium) for 2-3 days after splitting. At this time, the cells were 50-60% confluent and the medium was exchanged with unconditioned SR medium containing 1% DMSO.

The cultures were fed daily with SR medium for 4 days and then exchanged into unconditioned SR medium containing 2.5% Na-butyrate (which was previously identified as a hepatocyte differentiation agent). The cultures were fed daily with this medium for 6 days; at which time one half of the cultures were evaluated by immunocytochemistry. The other half of the cultures were harvested with trypsin and replated onto collagen, to further promote enrichment for hepatocyte lineage cells. Immunocytochemistry was then performed on the following day.

As shown in Table 1, the cells which underwent the final re-plating had ~5-fold higher albumin expression, similar $\alpha_1$-antitrypsin expression and 2-fold less cytokeratin expression than the cells not re-plated. The secondary plating for the cells is believed to enrich for the hepatocyte-like cells.

TABLE 1

Phenotype of Differentiated Cells

| Antibody Specificity | No trypsinization % positive | Trypsinization % positive |
|---|---|---|
| (no primary antibody) | 0 | 0 |
| (IgG1 control) | 0 | 0 |
| albumin | 11% | 63% |
| $\alpha_1$-antitrypsin | >80% | >80% |
| α-fetoprotein | 0 | 0 |
| Cytokeratin 8 | >80% | 45% |
| Cytokeratin 18 | >80% | 30% |
| Cytokeratin 19 | >80% | 30% |
| glycogen | 0 | >50% |

Adjustments to culture conditions are shown in Table 2. Hepatocyte Culture Medium is purchased from Clonetics; Strom's Medium is prepared as described in Runge et al., Biochem. Biophys. Res. Commun. 265:376, 1999. The cell populations obtained are assessed by immunocytochemistry and enzyme activity.

TABLE 2

Direct Differentiation Protocols

| Undifferentiated cells (until confluent) | Pre-differentiation (4 days) | Hepatocyte induction (6 days) | Further differentiation (Groups 1-3 only; 4 days) |
|---|---|---|---|
| Feeder-free conditions | 20% SR medium + 1% DMSO | 20% SR medium + 1% DMSO + 2.5 mM butyrate | HCM + 30 ng/mL hEGF + 10 ng/mL TGF-α + 30 ng/mL HGF + 1% DMSO + 2.5 mM butyrate |
| Feeder-free conditions | 20% SR medium + 1% DMSO | 20% SR medium + 1% DMSO + 2.5 mM butyrate | 20% SR medium + 30 ng/mL hEGF + 10 ng/mL TGF-α + 30 ng/mL HGF + 1% DMSO + 2.5 mM butyrate |

TABLE 2-continued

Direct Differentiation Protocols

| Undifferentiated cells (until confluent) | Pre-differentiation (4 days) | Hepatocyte induction (6 days) | Further differentiation (Groups 1-3 only; 4 days) |
|---|---|---|---|
| Feeder-free conditions | 20% SR medium + 1% DMSO | 20% SR medium + 1% DMSO + 2.5 mM butyrate | Strom's medium + 30 ng/mL hEGF + 10 ng/mL TGF-α + 30 ng/mL HGF + 1% DMSO + 2.5 mM butyrate |
| Feeder-free conditions | 20% SR medium + 1% DMSO | HCM + 30 ng/mL hEGF + 10 ng/mL TGF-α + 30 ng/mL HGF + 1% DMSO + 2.5 mM butyrate | |
| Feeder-free conditions | 20% SR medium + 1% DMSO | 20% SR medium + 30 ng/mL hEGF + 10 ng/mL TGF-α + 30 ng/mL HGF + 1% DMSO + 2.5 mM butyrate | |
| Feeder-free conditions | 20% SR medium + 1% DMSO | Strom's medium + 30 ng/mL hEGF + 10 ng/mL TGF-α + 30 ng/mL HGF + 1% DMSO + 2.5 mM butyrate | |
| Feeder-free conditions | HCM + 30 ng/mL hEGF + 10 ng/mL TGF-α + 30 ng/mL HGF + 1% DMSO | HCM + 30 ng/mL hEGF + 10 ng/mL TGF-α + 30 ng/mL HGF + 1% DMSO + 2.5 mM butyrate | |
| Feeder-free conditions | 20% SR medium + 30 ng/mL hEGF + 10 ng/mL TGF-α + 30 ng/mL HGF + 1% DMSO | 20% SR medium + 30 ng/mL hEGF + 10 ng/mL TGF-α + 30 ng/mL HGF + 1% DMSO + 2.5 mM butyrate | |
| Feeder-free conditions | Strom's medium + 30 ng/mL hEGF + 10 ng/mL TGF-α + 30 ng/mL HGF + 1% DMSO | Strom's medium + 30 ng/mL hEGF + 10 ng/mL TGF-α + 30 ng/mL HGF + 1% DMSO + 2.5 mM butyrate | |

Other additives tested in the subsequent (4-day) maturation step include factors such as FGF-4, and oncostatin M in the presence of dexamethazone.

FIG. 2 shows the effect of HCM on maturation of hES-derived cells. Left column: 10× magnification; Right column: 40× magnification. By 4 days in the presence of butyrate, more than 80% of cells in the culture are large in diameter, containing large nuclei and granular cytoplasm (Row A). After 5 days in SR medium, the cells were switched to HCM. Two days later, many cells are multinucleated, and have a large polygonal shape (Row B). By 4 days in HCM, multinucleated polygonal cells are common, and have a darker cytosol (Row C), by which criteria they resemble freshly isolated human adult hepatocytes (Row D) or fetal hepatocytes (Row E).

Example 4

Microarray analysis of Expression by Undifferentiated and Differentiated Cells

An analysis of differential gene expression was performed by contrasting mRNA from undifferentiated H9 cultures with mRNA from corresponding EBs. The EBs were maintained in growth medium for 8 days, or kept in growth medium for 4 days, followed by 4 days of treatment with 0.5 µM retinoic acid. EBs were harvested after 2 d, 4 d, or 8 d and the resulting mRNA was compared directly with mRNA from undifferentiated cultures. This analysis tracks the transformation of a relatively homogenous cell population into a complex mix of differentiated cell types, and thus the readouts are affected both by the magnitude of the change in gene expression, and, in the case of expression changes specific to a differentiated cell type, by the representation of that cell type in the culture. The arrays used in these experiments sample approximately 10,000 cDNAs selected to represent a large portion of characterized human genes.

Total RNA was harvested from human ES cultures or their differentiated derivatives using the Qiagen RNAeasy™ Miniprep kit according to the manufacturer's instructions. RNA was quantified by measuring ultraviolet absorption at 260 nm. Poly A$^+$ mRNA was prepared from the total RNA preparations using Qiagen Oligotex™ Minipreps according to the instructions of the manufacturer. Final mRNA preparations were quantified by $A_{260}$ measurements, then visually inspected following electrophoresis on native agarose gels. Sample RNAs were sent to a contract laboratory (Incyte Pharmaceuticals, Palo Alto, Calif.) for conversion into Cy3- or Cy5 labeled cDNA probe, which was subsequently hybridized to UNIGEM™ 1.0 arrays.

Following processing of the hybridized arrays, fluorescence measurements were quantified and the results returned for analysis. Probe pairings were performed with samples from undifferentiated ES cells in the Cy3 channel, and the differentiated ES cell samples in the Cy5 channel. A change in expression (as measured by comparing the Cy3 and Cy5 channels) was generally considered significant if the difference was at least 2.5-fold.

FIG. 3 shows the expression analysis of embryoid body (EB) cells. The numbers in the matrix compare expression at the mRNA level with expression in the undifferentiated hES cell line from which the EBs were derived. Numbers 1.1 and above represent a proportional increase in expression in EB cells; numbers −1.1 and below represent a proportional decrease in expression. The four columns show results obtained from EBs in standard suspension culture for 2, 4, or 8 days; or cultured 4 days in regular medium and 4 days in medium containing retinoic acid (4 d−/4 d+).

The differentiation of hES cells involves the activation and repression of many genes, including ESTs with no known function. Interestingly, the addition of retinoic acid to the suspension culture for the final 4 days of differentiation had relatively minor effect on the gene expression pattern (compare 4 d−/4 d+ with 8 d).

Genes whose expression is reduced during differentiation sample a wide range of functions, including metallothioneins, growth factors (e.g., FGF9), secreted cysteine-rich proteins (e.g., osteopontin, AGF-BPS, Cyr61, connective tissue growth factor), the selenium donor protein selD, and many others. In general, the most significant alterations in expression occur after 4 days of suspension culture, and correspond with the onset of changes in cell morphologies. Of interest, the expression of two genes involved in the catabolism of α-D-Glucose phosphate, UDP-glucose phosphorylase and phosphoglucomutase, are dramatically reduced upon differentiation, suggesting a potential alteration in glucose metabolism.

The arrays used in these experiments do not contain cDNA features corresponding to hTERT; however, a marked decrease in the expression of the mRNA for TRF1 was observed. TRF1 is a principal telomere binding factor whose expression has been correlated with a shortening of telomere lengths. Thus, the expression of both positive (hTERT) and negative (TRF1) regulators of telomere length is reduced during ES cell differentiation.

Several genes associated with visceral endoderm and early hepatic differentiation were predominant in this analysis, including α-fetoprotein, apoplipoprotein A-II, apoplipoprotein AI regulatory protein-1, $\alpha_1$-antitrypsin, and the α, β, and γ chains of fibrinogen. This induction is apparent within 2 days of differentiation, and is not substantially affected by retinoid treatment. The induced expression of cellular retinoic acid binding proteins 1 and 2 (CRABP I, II) is not observed in retinoid treated cultures, consistent with a proposed negative feedback loop in which retinoids specifically inhibit the transcription of the promoter of the CRAB I gene.

Expression of the IL-6 receptor gp130 is low in hES cultures, and is induced upon differentiation. These results provide a molecular basis for the lack of LIF responsiveness in hES cultures (Thomson et al., 1999; Reubinoff et al., 2000) and indicate a substantially different role for gp130 in human vs. mouse ES cells, where LIF signaling is directly implied in the maintenance of the undifferentiated state.

Other differentiation-induced genes include the protein homologs pleiotropin and midkine. These secreted cytokine have proposed roles as mitogens for neuronal and hepatic cell types, or as generalized angiogenic factors (Owada et al., 1999; Sato et al., 1999), and as such may play a similar role in ES cell differentiation. The induction of DNA binding proteins, such as homeobox b5 protein and meis1, likely reflects the central role of transcriptional regulators in differentiation processes.

Example 5

Direct differentiation of hES Cells to Neurons

This study evaluated various paradigms for differentiating human ES cells into neurons without the formation of embryoid bodies.

A strategy was developed in which the test factors were placed into groups based on homology and/or functional redundancy (Table 3). Grouping factors increases the likelihood that an activity associated within that group will be elicited on the ES cell population. The hypothesis is that certain factors within the mixture will initiate a differentiation cascade. As differentiation proceeds, and the receptor expression profile of the cells change, they will become responsive to other factors in the mixture.

Providing a complex mixture of factors continuously over the treatment period avoids the need to define exactly how and when the responsiveness of the cells changes. When a mixture is identified that elicits the desired differentiation process, it can be systematically simplified to achieve a minimal optimal mixture. After further testing, minimal treatment may ultimately comprise one, two, three, or more of the factors listed, used either simultaneously or in sequence according to the empirically determined protocol.

TABLE 3

Test Factor Groups

| Group 1 | Group 2 | Group 3 |
|---|---|---|
| Neurotrophins | Mitogens | Stem Cell Factors |
| 30 ng/mL NGF | 30 ng/mL EGF | 8 ng/mL LIF |
| 30 ng/mL NT-3 | 30 ng/mL FGF-2 | 3 ng/mL IL-6 |
| 30 ng/mL NT-4 | 37 ng/mL FGF-8b | 3 ng/mL IL-11 |
| 30 ng/mL BDNF | 30 ng/mL IGF-I | 3 ng/mL SCF |
|  | 30 ng/mL PDGF-AA | 30 ng/mL CNTF |

| Group 4 | Group 5 | Group 6 |
|---|---|---|
| Differentiation Factors | TGF-β Superfamily Antagonists | Differentiation Factor |
| TGF-β Superfamily | 150 ng/mL Noggin | 37 ng/mL SHH |
| 30 ng/mL BMP-2 | 30 ng/mL Follistatin |  |
| 37 ng/mL GDF-5 |  |  |
| 3 ng/mL GDNF |  |  |
| 30 ng/mL Neurturin |  |  |

| Group 7 | Group 8 | Group 9 |
|---|---|---|
| Neurotrophic Factor | Differentiation Factor | Survival Factor/Antioxidant |
| 37 ng/mL Midkine | 17 μM Retinoic Acid | 166 μM Ascorbic Acid |

| Group 10 | Group 11 |
|---|---|
| Differentiation Factor/ Neurotransmitter | Survival Factor |
| 10 μM Dopamine | 100 μM Dibutyryl cAMP |

The experiment was conducted as follows. Monolayer cultures of a human ES cell line were harvested by incubating in Collagenase IV for 5-10 min, and then scraping the cells from the plate. The cells were dissociated by trituration and plated at subconfluence onto 96 well tissue culture plates pretreated with growth factor-reduced Matrigel® in Knockout DMEM medium (Gibco BRL) with Knockout Serum Replacement (Gibco BRL) conditioned 24 h by mouse embryonic fibroblasts. One day after plating, the medium was replaced with Neurobasal Medium (Gibco BRL) supplemented with 1 mM glutamine, B27 supplement (Gibco BRL) and groups of test factors as described below. The cells were fed daily with fresh Neurobasal Medium containing glutamine, B27, and test factors for 11 days.

After 11 days, the cells were harvested by incubation in trypsin for 5-10 min, replated at a 1:6 dilution onto 96 well tissue culture plates pretreated with laminin, and fed daily with fresh Neurobasal Medium containing glutamine, B27 and test factors for an additional 5 days. Cells were fixed for 20 min in 4% paraformaldehyde, and stained with antibodies to the early neuronal marker, β-Tubulin-III, the late neuronal marker, MAP-2, and tyrosine hydroxylase, an enzyme associated with dopaminergic neurons. Cell nuclei were labeled with DAPI, and quantified by visual inspection. Results are shown in Table 4.

TABLE 4

Direct Differentiation of hES Cells to Neurons

| Test Compound Groups Included in Cell Culture | βTubulin-III positive Cells/Well | % Total | MAP-2 positive Cells/Well | Tyrosine Hydroxylase positive Cells/Well | % Total |
|---|---|---|---|---|---|
| Control | 102 | — | 2 | 1 | — |
| Treatment A: 1, 2, 3, 4, 6, 7, 8, 9, 10, 11 | 0 | 0 | 0 | 0 | — |
| Treatment B: 1, 2, 3, 5, 6, 7, 8, 9, 10, 11 | 362 | 6% | 132 | 14 | 0.2% |
| Treatment C: 1, 2, 4, 6, 7, 8, 9, 10, 11 | — | — | — | — | — |
| Treatment D; 1, 2, 5, 6, 7, 8, 9, 10, 11 | 378 | 11% | 162 | 16 | 0.5% |
| Treatment E: 1, 3, 4, 6, 7, 8, 9, 10, 11 | 6 | — | 2 | 4 | — |
| Treatment F: 1, 3, 5, 6, 7, 8, 9, 10, 11 | 282 | 12% | 92 | 4 | 0.2% |
| Treatment G; 1, 4, 6, 7, 8, 9, 10, 11 | 17 | — | 0 | 2 | — |

— = not determined

In another experiment, cells were cultured in Neurobasal medium supplemented with glutamine, B27 and groups of test factors as before, harvested with trypsin at 8 days, and replated for 5 days. Results are shown in Table 5.

TABLE 5

Direct Differentiation of hES Cells to Neurons

| Test Compound Groups Included in Cell Culture | βTubulin-III positive Cells/Well | MAP-2 positive Cells/Well | Tyrosine Hydroxylase positive Cells/Well | Percent of MAP-2 positive cells also positive for TH |
|---|---|---|---|---|
| Control | 4 | 4 | 0 | |
| Treatment A: 1, 2, 3, 4, 6, 7, 8, 9, 10, 11 | 12 | 8 | 3 | |
| Treatment B: 1, 2, 3, 5, 6, 7, 8, 9, 10, 11 | 268 | 12 | 4 | |
| Treatment C: 1, 2, 4, 6, 7, 8, 9, 10, 11 | 12 | 0 | 0 | |
| Treatment D: 1, 2, 5, 6, 7, 8, 9, 10, 11 | 372 | 48 | 7 | 15% |
| Treatment E: 1, 3, 4, 6, 7, 8, 9, 10, 11 | 0 | 0 | 0 | |
| Treatment F: 1, 3, 5, 6, 7, 8, 9, 10, 11 | 196 | 56 | 0 | |
| Treatment G: 1, 4, 6, 7, 8, 9, 10, 11 | 16 | 0 | 9 | |

Several treatment paradigms induced the direct differentiation of neurons. Treatments that included Group 5 factors (noggin and follistatin) were the most effective.

FIG. 4 shows exemplary fields of differentiated cells obtained using Treatment B, Treatment D, and Treatment F, and stained for β-tubulin-III. About 5-12% of the cells are neurons, based on morphology and β-tubulin-III staining. About ⅓ of these are mature neurons, based on MAP-2 staining. About 2-5% of total neurons (5-15% of MAP-2 positive neurons) also stained for tyrosine hydroxylase, which is consistent with a dopaminergic phenotype.

It will be recognized that the compositions and procedures provided in the description can be effectively modified by those skilled in the art without departing from the spirit of the invention embodied in the claims that follow.

The invention claimed is:

1. A method for producing a neural cell population from human embryonic stem (hES) cells, comprising:
   a) obtaining a population of hES cells;
   b) optionally initiating differentiation of the hES cells into a heterogeneous population of precursor cells; and
   c) culturing the hES cells from step a) or precursor cells from step b) in a medium containing noggin and/or follistatin so as to produce a neural cell population wherein at least 5% of the neural cells express β-tubulin lll.

2. The method of claim 1, comprising culturing the hES cells in a medium containing noggin and/or follistatin so as to produce a neural cell population in which about ⅓ of the β-tubulin lll expressing cells further express microtubule-associated protein 2 (MAP-2).

3. The method of claim 1, comprising initiating differentiation of the hES cells into a heterogeneous population of precursor cells, and then culturing the initiated cells in a medium containing noggin and/or follistatin so as to produce a neural cell population in which about ⅓ of the β-tubulin lll expressing cells further express MAP-2.

4. The method of claim 1, wherein the medium further contains a neurotrophin.

5. The method of claim 4, wherein the neurotrophin is neurotrophin 3 (NT-3) or brain derived neurotrophic factor (BDNF).

6. The method of claim 1, wherein the medium further contains a combination of factors selected from differentiation factors, neurotrophic factors, and survival factors.

7. The method of claim 2, comprising initiating differentiation of the hES cells by plating them onto a solid surface without forming embryoid bodies or cell aggregates.

8. The method of claim 7, wherein the solid surface comprises fibronectin.

9. The method of claim 1, further comprising combining the neural cell population with a compound, determining any phenotypic or metabolic changes in the neural cells that result from contact with the compound, and correlating the change with cellular toxicity or modulation caused by the compound.

10. The method of claim 1, further comprising compounding the neural cell population as a pharmaceutical composition.

* * * * *

SEQUENCE LISTING

<160> NUMBER OF SEQ ID NOS: 4

<210> SEQ ID NO 1
<211> LENGTH: 25

```
<212> TYPE: DNA
<213> ORGANISM: Homo sapiens
<220> FEATURE:
<221> NAME/KEY: primer_bind
<222> LOCATION: (1)..(25)

<400> SEQUENCE: 1
cttgctgcag aagtgggtgg aggaa                                           25

<210> SEQ ID NO 2
<211> LENGTH: 21
<212> TYPE: DNA
<213> ORGANISM: Homo sapiens
<220> FEATURE:
<221> NAME/KEY: primer_bind
<222> LOCATION: (1)..(21)

<400> SEQUENCE: 2
ctgcagtgtg ggtttcgggc a                                               21

<210> SEQ ID NO 3
<211> LENGTH: 20
<212> TYPE: DNA
<213> ORGANISM: Homo sapiens
<220> FEATURE:
<221> NAME/KEY: primer_bind
<222> LOCATION: (1)..(20)

<400> SEQUENCE: 3
cggaagagtg tctggagcaa                                                 20

<210> SEQ ID NO 4
<211> LENGTH: 19
<212> TYPE: DNA
<213> ORGANISM: Homo sapiens
<220> FEATURE:
<221> NAME/KEY: primer_bind
<222> LOCATION: (1)..(19)

<400> SEQUENCE: 4
ggatgaagcg gagtctgga                                                  19
```